(12) United States Patent
dos Santos et al.

(10) Patent No.: US 10,155,953 B2
(45) Date of Patent: Dec. 18, 2018

(54) EXPRESSION CARTRIDGE FOR THE TRANSFORMATION OF EUKARYOTIC CELLS, METHOD FOR TRANSFORMING EUKARYOTIC CELLS, GENETICALLY MODIFIED ORGANISM, METHOD FOR PRODUCING BIOFUELS AND/OR BIOCHEMICALS, AND THUS PRODUCED BIOFUEL AND/OR BIOCHEMICAL

(71) Applicant: Biocelere Agroindustrial Ltda., Campinas (BR)

(72) Inventors: Leandro Vieira dos Santos, São Paulo (BR); Gonçalo Amarante Guimarães Pereira, Campinas (BR)

(73) Assignee: Biocelere Agroindustrial Ltda., Campinas (BR)

( * ) Notice: Subject to any disclaimer, the term of this patent is extended or adjusted under 35 U.S.C. 154(b) by 0 days.

(21) Appl. No.: 15/315,081

(22) PCT Filed: Jun. 12, 2015

(86) PCT No.: PCT/BR2015/050075
§ 371 (c)(1),
(2) Date: Nov. 30, 2016

(87) PCT Pub. No.: WO2015/188244
PCT Pub. Date: Dec. 17, 2015

(65) Prior Publication Data
US 2017/0114350 A1    Apr. 27, 2017

(30) Foreign Application Priority Data
Jun. 12, 2014 (BR) .............................. 102014014407

(51) Int. Cl.
| | |
|---|---|
| *C12N 1/19* | (2006.01) |
| *C12N 9/92* | (2006.01) |
| *C12N 15/81* | (2006.01) |
| *C12P 7/06* | (2006.01) |
| *C12N 15/52* | (2006.01) |

(52) U.S. Cl.
CPC ............... *C12N 15/81* (2013.01); *C12N 9/92* (2013.01); *C12N 15/52* (2013.01); *C12P 7/06* (2013.01); *C12Y 503/01005* (2013.01); *Y02E 50/17* (2013.01)

(58) Field of Classification Search
None
See application file for complete search history.

(56) References Cited

U.S. PATENT DOCUMENTS

| | | |
|---|---|---|
| 6,410,302 B1 | 6/2002 | Traff |
| 8,399,215 B2 | 3/2013 | Klaassen |

FOREIGN PATENT DOCUMENTS

| | | |
|---|---|---|
| EP | 2679686 A1 | 1/2014 |
| WO | 2006009434 A1 | 1/2006 |
| WO | 2011153516 A2 | 12/2011 |
| WO | 2014018552 A1 | 1/2014 |

OTHER PUBLICATIONS

A. Madhavan et al. "Xylose isomerase from polycentric fungus *Orpinomyces*: gene sequencing, cloning, and expression in *Saccharomyces cerevisiae* for bioconversion of xylose to ethanol", Appl. Microbiol. Biotechnol. 82:1067-1078 (2009).*

* cited by examiner

*Primary Examiner* — Rebecca E Prouty
(74) *Attorney, Agent, or Firm* — Laurence P. Colton; Smith Tempel Blaha LLC

(57) ABSTRACT

The present invention describes the expression cassette for transforming eukaryotic cell which comprises the peptide encoding non-natural sequence of nucleotides with xylose isomerase feature (SEQ ID NO: 1), optionally also comprising other genes of pentose phosphate route. Additionally, it is described the microorganism filed under the number DSM28739, which, in addition to the above-mentioned modifications, also present genetic modifications from adaptive evolution. The described microorganism shows efficient consumption of xylose and conversion of ethanol when compared to its correspondent without said genetic modifications and mutations from evolution. It is also described the process for producing biofuels e biochemicals, preferably ethanol, mainly from the lignocellulosic portion of the vegetal biomass. Biofuels, preferably ethanol, and biochemicals produced by the process of the invention are also described.

1 Claim, 5 Drawing Sheets
Specification includes a Sequence Listing.

```
TCGAGGAGAACTTCTAGTATATCCACATACCTAATATTATTGCCTTATTAAAAATGGAATCCCA
ACAATTACATCAAAATCCACATTCTCTTCAAAATCAATTGTCCTGTACTTCCTTGTTCATGTGT
GTTCAAAAACGTTATATTTATAGGATAATTATACTCTATTTCTCAACAAGTAATTGGTTGTTTG
GCCGAGCGGTCTAAGGCGCCTGATTCAAGAAATATCTTGACCGCAGTTAACTGTGGGAATACTC
AGGTATCGTAAGATGCAAGAGTTCGAATCTCTTAGCAACCATTATTTTTTCCTCAACATAACG
AGAACACACAGGGGCGCTATCGCACAGAATCAAATTCGATGACTGGAAATTTTTTGTTAATTTC
AGAGGTCGCCTGACGCATATACCTTTTTCAACTGAAAAATTGGGAGAAAAAGGAAAGGTGAGAG
GCCGGAACCGGCTTTTCATATAGAATAGAGAAGCGTTCATGACTAAATGCTTGCATCACAATAC
TTGAAGTTGACAATATTATTTAAGGACCTATTGTTTTTTCCAATAGGTGGTTAGCAATCGTCTT
ACTTTCTAACTTTTCTTACCTTTTACATTTCAGCAATATATATATATATTTCAAGGATATACCA
TTCTAATGTCTGCCCCTAAGAAGATCGTCGTTTTGCCAGGTGACCACGTTGGTCAAGAAATCAC
AGCCGAAGCCATTAAGGTTCTTAAAGCTATTTCTGATGTTCGTTCCAATGTCAAGTTCGATTTC
GAAAATCATTTAATTGGTGGTGCTGCTATCGATGCTACAGGTGTCCCACTTCCAGATGAGGCGC
TGGAAGCCTCCAAGAAGGTTGATGCCGTTTTGTTAGGTGCTGTGGGTGGTCCTAAATGGGGTAC
CGGTAGTGTTAGACCTGAACAAGGTTTACTAAAAATCCGTAAAGAACTTCAATTGTACGCCAAC
TTAAGACCATGTAACTTTGCATCCGACTCTCTTTTAGACTTATCTCCAATCAAGCCACAATTTG
CTAAAGGTACTGACTTCGTTGTTGTCAGAGAATTAGTGGGAGGTATTTACTTTGGTAAGAGAAA
GGAAGACGATGGTGATGGTGTCGCTTGGGATAGTGAACAATACACCGTTCCAGAAGTGCAAAGA
ATCACAAGAATGGCCGCTTTCATGGCCCTACAACATGAGCCACCATTGCCTATTTGGTCCTTGG
ATAAAGCTAATGTTTTGGCCTCTTCAAGATTATGGAGAAAAACTGTGGAGGAAACCATCAAGAA
CGAATTCCCTACATTGAAGGTTCAACATCAATTGATTGATTCTGCCGCCATGATCCTAGTTAAG
AACCCAACCCACCTAAATGGTATTATAATCACCAGCAACATGTTTGGTGATATCATCTCCGATG
AAGCCTCCGTTATCCCAGGTTCCTTGGGTTTGTTGCCATCTGCGTCCTTGGCCTCTTTGCCAGA
CAAGAACACCGCATTTGGTTTGTACGAACCATGCCACGGTTCTGCTCCAGATTTGCCAAAGAAT
AAGGTTGACCCTATCGCCACTATCTTGTCTGCTGCAATGATGTTGAAATTGTCATTGAACTTGC
CTGAAGAAGGTAAGGCCATTGAAGATGCAGTTAAAAAGGTTTTGGATGCAGGTATCAGAACTGG
TGATTTAGGTGGTTCCAACAGTACCACCGAAGTCGGTGATGCTGTCGCCGAAGAAGTTAAGAAA
ATCCTTGCTTAAAAAGATTCTCTTTTTTATGATATTTGTACATAAACTTTATAAATGAAATTC
ATAATAGAAACGACACGAAATTACAAAATGGAATATGTTCATAGGGTAGACGAAACTATATACG
CAATCTACATACATTTATCAAGAAGGAGAAAAAGGAGGATAGTAAAGGAATACAGGTAAGCAAA
TTGATACTAATGGCTCAACGTGATAAGGAAAAAGAATTGCACTTTAACATTAATATTGACAAGG
AGGAGGGCACCACACAAAAAGTTAGGTGTAACAGAAAATCATGAAACTACGATTCCTAATTTGA
TATTGGAGGATTTTCTCTAAAAAAAAAAAAATACAACAAATAAAAAACACTCAATGACCTGACC
ATTTGATGGAGTTTAAGTCAATACCTTCTTGAACCATTTCCCATAATGGTGAAAGTTCCCTCAA
GAATTTTACTCTGTCAGAAACGGCCTTACGACGTAGTCGA
```

Figure 5

EXPRESSION CARTRIDGE FOR THE TRANSFORMATION OF EUKARYOTIC CELLS, METHOD FOR TRANSFORMING EUKARYOTIC CELLS, GENETICALLY MODIFIED ORGANISM, METHOD FOR PRODUCING BIOFUELS AND/OR BIOCHEMICALS, AND THUS PRODUCED BIOFUEL AND/OR BIOCHEMICAL

FIELD OF THE INVENTION

The present invention refers to biofuels, biochemicals and to processes for obtaining them. More specifically, the present invention provides technical solutions for producing second-generation fuels based on conversion of vegetal biomass, preferably from polymers of the vegetal cellular wall. Among other objects, the present technology describes an expression cassette for transforming eukaryotic cells and genetically modified microorganism, with efficient fermentative performance in the conversion of sugars present in vegetal biomass into biochemicals and/or biofuels. The microorganism of the present invention passed by the process of improvement by evolutionary engineering in order to increase its consumption of xylose, thus favoring its performance in industrial scale. A process for obtaining biofuels and/or biochemicals and the products thus obtained are also described.

BACKGROUND OF THE INVENTION

The need for replacement of world matrix of fuels based on fossil sources by renewable alternatives made the production of second-generation fuels, for example, ethanol, one of the most promising technologies in development phase. This process consists of conversion of polymers which form the vegetal biomass, mainly those present in cellular wall as cellulose, hemicellulose and lignin, into biofuels and/or biochemicals.

The vegetal biomass is a complex mixture of chemically distinct compounds which can be fractionated generating components with specific applications. Thus, in the same way a petrochemical refinery produces a great variety of products derived from crude oil, the same principles can be applied to biorefineries, that is, refineries based on biomass (Santos, L. V.; Pereira, G. A. G. Petroquimica verde—Anais do Simpésio Microrganismos em Agroenergia: da Prospecç ao aos Bioprocessos. Editora Embrapa. ISSN 2177-4439, 2013).

Although the use of vegetal biomass as a source of fermentable sugars is a promising and sustainable alternative, some challenges need to be overcome, like the availability of sugar from vegetal cellular wall. This procedure may be done through the action of hydrolytic enzymes (cellulases and hemicellulases), which provide the monomers of sugars (hexoses and pentoses) which are posteriorly metabolized by microorganisms for generating biochemicals and biofuels.

However, microorganisms naturally able to consume sugars present in the cellulose and hemicellulose chains, generally, are not efficiently usable in industrial scale. Thus, it is necessary to develop microorganisms with ability to use efficiently these sugars of vegetal cellular wall in industrial scale, as described in the present invention.

The use of microorganisms as efficient platforms in the conversion of biomass sugar into high added value products is widely described. In this sense, the yeast *Saccharomyces cerevisiae* has received prominent role due to its robustness and tolerance in industrial fermentation conditions. The ease of genetic manipulation of this organism and the use of metabolic engineering tools, in synergy with biology of systems and synthetic biology, has allowed the inclusion of new metabolic routes for producing fuels and chemicals such as ethanol, biobutanol, biodiesel, 1,2-propanediol, succinic acid, pyruvic acid, among others [Cellular and Molecular Life Sciences, 69(16):2671-90, 2012].

Wild lines of *S. cerevisae* are not naturally able to ferment pentoses, such as, for example, xylose, present in biomass. However, several studies have already done procedures of metabolic engineering in *S. cerevisiae* through the introduction in these organisms of metabolic routes for consumption of xylose, focusing on two main routes: the Xylose Reductase route—Xylitol Dehydrogenase (XR-XDH) and Xylose Isomerase (XI) route.

Among the studies carried out, the introduction of gene which encodes the xylose isomerase (XI) enzyme allows the strain to present higher yield in the production of alcohol and/or acids than when it is modified with other gene, as for example, gene encoding xylose reductase or xylitol dehydrogenase, since there is less accumulation of undesirable byproducts, such as xylitol and glycerol [2004, FEMS Yeast Res. 4: 655-664].

The XR-XDH route, present in microorganisms eukaryotes, consists of two redox reactions, where xylose is reduced to xylitol by the action of xylose reductase (XR) enzyme, in a reaction mediated by NADPH/NADH and then, xylitol is oxidized to xylulose through the xylitol dehydrogenase (XDH) enzyme, exclusively mediated by $NAD^+$. The NADPH co-factor is mainly regenerated in the oxidative phase of the pentose phosphate route, producing $CO_2$. In addition, $NAD^+$ is regenerated mainly in the respiratory chain, with the $O_2$ as final acceptor of electrons. Under limited oxygen concentrations, the complete reoxidation of $NAD^+$ does not occur, resulting in a redox unbalance and the accumulation of xylitol, which directly impacts the final yield of ethanol [Biochemical Engineering Journal, Amsterdam, v. 12, n. 1, p. 49-59, 2002]. In addition to xylitol, other byproduct formed is glycerol, due to re-oxidation of excess NADH through XDH [FEMS Yeast Research, Delft, v. 4, n. 6, p. 655-664, 2004].

The xylose isomerase (XI) route, more common in prokaryotes, occurs in a single step, avoiding redox unbalance and the formation of byproducts that decrease the yield of ethanol. For several decades, attempts at heterologous expression of bacterial XI in *S. cerevisiae* were not successful [Enzyme and Microbial Technology, Amsterdam, v. 32, n. 2, p. 252-259, 2003]. In 2003, the functional expression in *S. cerevisiae* of a xylose isomerase of anaerobic fungus *Piromyces* sp. [FEMS Yeast Research, Delft, v. 4, n. 1, p. 69-78, 2003] and in 2009 of *Orpiromyces* sp. fungus [Applied Microbiology and Biotechnology, Heidelberg, v. 82, n. 6, p. 1067-1078, 2009], resulted in mutants able to grow in xylose as the only source of carbon, with high activities of these enzymes, higher yield in the production of ethanol, lower production and accumulation of intermediate metabolites and with less catabolic repression in medium containing glucose and xylose [FEMS Yeast Research, Delft, v. 4, n. 6, p. 655-664, 2004; FEMS Yeast Research, Delft, v. 5, n. 4, p. 399-409, 2005a; FEMS Yeast Research, Delft, v. 5, n. 10, p. 925-934, 2005b]. The XR-XDH route has higher initial productivity for producing ethanol more rapidly, only with the insertion of the genes responsible for conversion of xylose, however, the XI route has a higher yield for not accumulating byproducts [Microbial Cell Factories, Londres, v. 6, n. 5, p. 1-10, 2007].

Many documents, as, for example, W02006/009434, WO2011/153516, U.S. Pat. No. 8,399,215, EP2679686 and WO2014018552 describe microorganisms able to use pentoses, more specifically xylose, as a source of carbon. In order to be able to consume xylose, it is necessary that the microorganism is genetically modified at least with the addition of the gene encoding xylose isomerase. As a strategy to improve yeast productivity, the genes encoding Xylulokinase and the genes of the pentoses phosphate route can be overexpressed: Transketolase, ribose 5-phosphate isomerase, ribose 5-phosphate epimerase and Transaldolase. Furthermore, the inactivation of the gene encoding an aldose reductase (GRE3) can be performed, aiming for a lower accumulation of xylitol and a higher yield of ethanol.

Therefore, the literature shows that increased expression of the genes described above that favor the conversion of xylose to ethanol is necessary for the consumption of this sugar is efficient. Thus, the microorganisms described in the prior art, which were genetically modified for consumption of xylose, can have (but not necessarily) the genetic modifications described above. What basically differentiates the efficiency and productivity in the anaerobic conversion of xylose in biofuels and/or biochemicals presented by each one of these is the form and location how these genes are incorporated to the microorganism genome, considering the best possible combination between these genes and respective promoters by which they are regulated, as well as the appropriate choice by the sequence of nucleotides encoding xylose isomerase, being this the main gene that, when expressed, enables the consumption of xylose for each modified microorganism, in addition to adaptation of microorganism through evolution. Thus, the present invention shows advantageously better yield and productivity than the microorganisms previously described in the prior art.

The present invention describes, among other objects, a genetically modified microorganism for inclusion of genes of the pentose phosphate route, as well as those of Xylulokinase, and inactivation of the aldose reductase gene, as described in the documents WO2006/009434, WO2011/153516, U.S. Pat. No. 8,399,215, EP2679686 and WO2014018552. The genetically modified microorganism of the present invention differs advantageously from the previous one by the fact that the genes have been more efficiently combined with their promoters, as well as inserted into more convenient location in the microorganism genome, when compared to the previously mentioned documents. Additionally, the gene encoding xylose isomerase herein inserted has been optimized, by the inventors, for the preferably codons of microorganism in which it was first inserted, in this case, the microorganism of *Saccharomyces cerevisiae* species. In the present document, the genes are inserted into the microorganism through the homologous recombination, then going to interact with its genome.

Specifically, referring to the production of ethanol, the obtaining of some lines able to act in industrial scale was successful. However, such strains are still susceptible to have their fermentative performance compromised or even be replaced by wild lines when subjected to the stressful conditions of the Brazilian process of ethanol production.

In the Brazilian fermentative process for ethanol production, it is usual that the plants do the intensive reuse of yeast cells used in the fermentation, process known as recycling. In this process, up to 90% of yeasts may be reused from one fermentation to another, resulting in very high cell densities inside the fermenter and making the fermentation time very short [FEMS yeast research, 8(7):1155-63, 2008].

In some industrial pants, the recycling can occur throughout the period harvest, lasting up to nine months. Thus, the prolonged period of recycling added to continuous input of microbial contaminants into the system, makes the fermentation environment highly competitive, imposing severe biotic and abiotic tensions on the strains of yeast used in the process [International Sugar Journal, Londres, v. 112, p. 86-89, 2010]. This competitive environment results in the replacement of yeasts which started the fermentation process by wild yeasts. This fact happens because the wild yeasts naturally occur in sugarcane and, therefore, are inserted together with it in the process of fermentation, thus ending up contaminating the entire industrial process [FEMS yeast research, 8(7):1155-63, 2008].

Additionally, some studies demonstrated that those yeasts that started the fermentation process, and ended up being replaced by the wild, are also not able to survive stressful situations of the industrial process of fermentation, such as high concentration of ethanol, high temperature, osmotic stress due to salts and sugars, acidity, sulfites and bacterial contamination [FEMS yeast research, 8(7):1155-63, 2008]. Thus, the obtaining of line with efficient capacity of resistance to the aggressive industrial process of fermentation, as well as susceptible to genetic modifications to acquire characteristics of interest, such as the consumption of pentoses, more specifically xylose, is not a trivial process.

The microorganism described in the present invention, therefore, is advantageously adapted to the Brazilian process of industrial fermentation and is shown to be differentially efficient in the conversion of sugars from vegetal biomass, mainly lignocellulosic material, to biofuels and/or biochemicals, that is, with sufficient yield to be applied in industrial scale, even under the stressful conditions of the Brazilian fermentation process.

Additionally, the microorganism described in the present invention shows features of industrial interest such as: being a non-flocculating strain, presenting high yield of ethanol, low formation of glycerol and xylitol, high viability, high growth rate, non-production of foam, among others.

BRIEF DESCRIPTION OF THE INVENTION

It is one of the objects of the present invention an expression cassette for transforming eukaryotic cell characterized in that it comprises:
a) at least one nucleotide sequence selected from the group consisting of: xylose isomerase (SEQ ID NO: 1), transaldolase (SEQ ID NO: 5), ribose 5-phosphate isomerase (SEQ ID NO: 7), xylulokinase (SEQ ID NO: 9), transcetolase (SEQ ID NO: 11) and ribose 5-phosphate epimerase (SEQ ID NO: 12);
b) at least one promoter nucleotide sequence selected from the group consisting of: promoter glyceraldehyde 3-phosphate dehydrogenase (SEQ ID NO: 2), promoter 3-phosphate kinase (SEQ ID NO: 6), promoter of alcohol dehydrogenase enzyme 1 (SEQ ID NO: 8);
c) at least one terminator nucleotide sequence selected from the group consisting of: terminator glyceraldehyde 3-phosphate dehydrogenase (SEQ ID NO: 3), terminator alcohol dehydrogenase (SEQ ID NO: 10), terminator 3-phosphate kinase (SEQ ID NO: 13);
and wherein the nucleotide sequence defined in a) is functionally linked to the promoter nucleotide sequence defined in b) and to the terminator nucleotide sequence defined in c), being heterologous any one of said sequences.

It is another object of the present invention a process for transforming eukaryotic cell comprising the introduction, in the cell to be transformed, of at least an expression cassette as defined by the present invention.

It is another object of the present invention a genetically modified microorganism comprising at least an expression cassette as defined by the present invention.

It is another object of the present invention the genetically modified microorganism *Saccharomyces cerevisiae* DSM28739.

It is another object of the present invention a process for producing biofuels and/or biochemicals which comprise the step of cultivation of microorganism as defined by the present invention.

It is another object of the present invention the biofuel that is obtained by the process as defined by the present invention.

It is another object of the present invention the biochemical which is obtained by the process as defined by the present invention.

The present invention describes a genetically modified microorganism with efficient fermentative performance in the conversion of sugars contained in vegetal biomass, in biofuels and/or biochemicals, when compared to its version without the genetic modifications described in the present document. More specifically, the genetically modified microorganism described in the present invention refers to any eukaryotic cell susceptible of genetic transformation, which can consist of yeasts or filamentous fungi, preferably yeast of *Saccharomyces* genus.

The microorganism of the invention provides efficient performance in the conversion of sugars present in the vegetal biomass, preferably lignocellulosic material, in biochemicals and/or biofuels. Thusr, in one embodiment, the present invention describes a microorganism of the *Saccharomyces cerevisiae* species more efficient that its correspondent without the genetic modifications in the conversion of pentoses present in the lignocellulosic material in alcohols and/or biochemicals, such as, for example, succinic acid, malic acid, 1,3-propanediol, 1,2-propanediol, butanol, isobutanol, biodiesel, 1,4-butanediol, 2,3-butanediol, PHB—poly(butyrate hydroxide), however, without being restricted to these, without however being restrict to it.

The microorganism described in the present invention is genetically modified by the introduction of sequence of nucleotides encoding a peptide with xylose isomerase function. This sequence was originally described in *Orpinomyces* sp. [Appl Microbiol Biotechnol, 82:1067-1078, 2009] (XI, EC 5.3.1.5) and manually optimized by the present inventors for the codons preferably used for *Saccharomyces cerevisiae*. The optimization comprises comparison between codons present in the sequence of Orpinomyces with those preferably used for *Saccharomyces* aiming to replace the same keeping, however, the proportion of codons present in *Saccharomyces*. The optimized sequence of xylose isomerase described in the present invention (represented in SEQ ID NO: 1) is, however, not natural and different from natural sequences of xylose isomerase already described. SEQ ID NO: 1 can also be useful for insertion in eukaryotic cell and expressed in its active form. The sequence of nucleotides SEQ ID NO: 1 can present in single copy or multiple copies in the genome.

The genetically modified host eukaryotic cell (target cell) may, additionally, contain genes of the pentose phosphate route, aiming increased speed of xylose conversion. However, Additionally to the insertion of SEQ ID NO: 1 in host cell, the present invention describes genetic modifications in the same cell aiming the favoring of metabolic flow through the pentose phosphate route, these modifications, however, not being a restrictive factor for transforming the host cell with the sequence of nucleotides represented in SEQ ID NO: 1.

In order to increase the flow of the phosphate pentoses route in the host cell, new copies of the genes encoding Xylulokinase enzymes are inserted (XKS1, EC 2.7.1.17), whose sequence of nucleotides is represented in this document by SEQ ID NO: 9, Transaldolase (TAL1, EC 2.2.1.2), represented by SEQ NO ID:5, Transcetolase (TKL1, EC 2.2.1.1), represented by SEQ ID NO: 11, Ribose 5-Phosphate Isomerase (RKI1, EC 5.3.1.6), represented by SEQ ID NO: 7; and Ribose 5-Phosphate Epimerase (RPE1, EC 5.1.3.1), represented by SEQ ID NO: 12.

Among the enzymes presented and which constitute the pentose-phospate route, at least one of the genes encoding them must be overexpressed and, preferably, linked to constitutive promoters, that is, those that are constantly expressed, regardless of the condition to which the cell is subjected, or naturally inducible promoters. In the present document, promoters are defined as a regulatory region, located in the 5' region of the gene under its action and responsible for the beginning of transcription, while terminators are defined as a sequence which determines the end of the gene during the transcription process.

The present invention further describes expression cassettes containing one or more endogenous enzymes genes from the non-oxidative phase of the pentoses phosphate route, for transforming eukaryotic cells. Such expression cassettes or gene constructs preferably comprise strong and constitutive promoters of the cell into which they will be inserted. Specifically, four embodiments of integrative expression cassettes constructed using strong and constitutive promoters of *Saccharomyces cerevisiae* and stably integrated into the host cell genome are described in the present specification.

One of the cassettes disclosed contains the gene encoding xylose isomerase, SEQ ID NO: 1 and is inserted into the host cell functionally linked and/or flanked, preferably, by the promoter and terminator region of the gene Glyceraldehyde 3-Phosphate Dehydrogenase, isoenzyme 1 (TDH1). A second cassette disclosed contains the gene encoding the enzyme Xylulokinase (SEQ ID NO: 9) is preferably constructed using the promoter and terminator of the gene encoding alcohol dehydrogenase enzyme (ADH1). A third cassette described in the present invention contains encoding genes of Transaldolase (SEQ NO ID:5) and Ribose 5-Phosphate Isomerase (SEQ ID NO: 7) and is constructed, preferably using promoters and terminators of the gene encoding the Glyceraldehyde 3-Phosphate Dehydrogenase enzyme, isoenzyme 1 (TDH1) to flank the gene of Transaldolase and promoters and terminators of 3-phosphoglycerate Kinase enzyme (PGK1) to flank the gene of Ribose 5-Phosphate Isomerase. The last cassette described in the present invention contains encoding genes of Transcetolase (SEQ ID NO: 11) and Ribose 5-Phosphate Epimerase (SEQ ID NO: 7). It is constructed, preferably, under the action of promoters and terminators of Glyceraldehyde 3-Phosphate Dehydrogenase genes, isoenzyme 1 (TDH1), flanking the gene of Transcetolase and promoter and terminator of gene encoding the 3-phosphoglycerate Kinase enzyme (PGK1).

Said expression cassettes with the genes of metabolic route of pentose phosphate favoring the consumption of xylose are introduced in the eukaryotic cell and respective genes are inserted in the target chromosome located between the centromere and the first gene adjacent to it, preferably in the region of 5 thousand first base pairs counted from the centromere both in the upstream and downstream direction, which may be even just upstream, just downstream or both simultaneously.

Additionally to the insertion of expression cassettes, the present invention describes the gene deletion GRE3 of host eukaryotic cell, which encodes an aldose reductase and is represented in SEQ ID NO: 14.

Furthermore, the present invention describes the stable integration and in high number of copies of cassette expressing XI (SEQ ID N:1) in the host cell genome. In the present document, it is considered high number of copies the insertion of, at least, 5 copies of the gene in question, the insertion of at least 20 copies being preferential.

The present document describes, therefore, a eukaryotic cell, preferably microorganism of *Saccharomyces cerevisiae* species, genetically modified containing in its genome at least one of genes of the enzymes needed to favor the non-oxidative part of the pentose phosphate routes, inserted preferably in high number of copies and in the region between the centromere and its first adjacent gene.

Additionally, a microorganism is described, which in addition to the above-represented genetic manipulation, was subjected to procedure of evolutionary engineering in order to generate random mutations which favor greater consumption of lignocellulosic portion of the vegetal biomass, preferably xylose in anaerobic medium and, accordingly, higher growth rate and higher production of biochemical compounds and/or biofuels, preferably ethanol, by time frame, when compared with the microorganism before the evolution process. The genetically modified microorganism described in the present invention presents differently the features of being non-flocculating, presenting high ethanol, yield, low glycerol and xylitol formation, high viability, high growth rate, non-production of foam, in addition to efficient ability of resistance to the aggressive fermentation process. This evolved microorganism was filed by the inventors in the German Collection of Microorganisms and Cell Culture-Leibniz-Institut DSMZ, having received the number DSM28739.

The microorganism DSM28739 described in the present invention shows features of industrial interest such as: being a non-flocculating strain, presenting high ethanol yield, low glycerol and xylitol formation, high viability, high growth rate, non-production of foam, among others.

Furthermore, the present invention describes the process of producing biofuels and biochemicals from vegetal biomass. More specifically, the process for producing biofuels and biochemicals preferably uses the lignocellulosic portion of the vegetal biomass. The process described in the present invention uses the microorganism of the invention, preferably DSM28739, for producing biofuels and/or biochemicals.

BRIEF DESCRIPTION OF THE DRAWINGS

In FIG. 5, it is shown the sequence of nucleotides represented as SEQ ID NO: 17, being indicated the region encoding LEU2 (underlined), along with its promoter and terminator (not underlined).

DETAILED DESCRIPTION OF THE INVENTION

Figure 1:
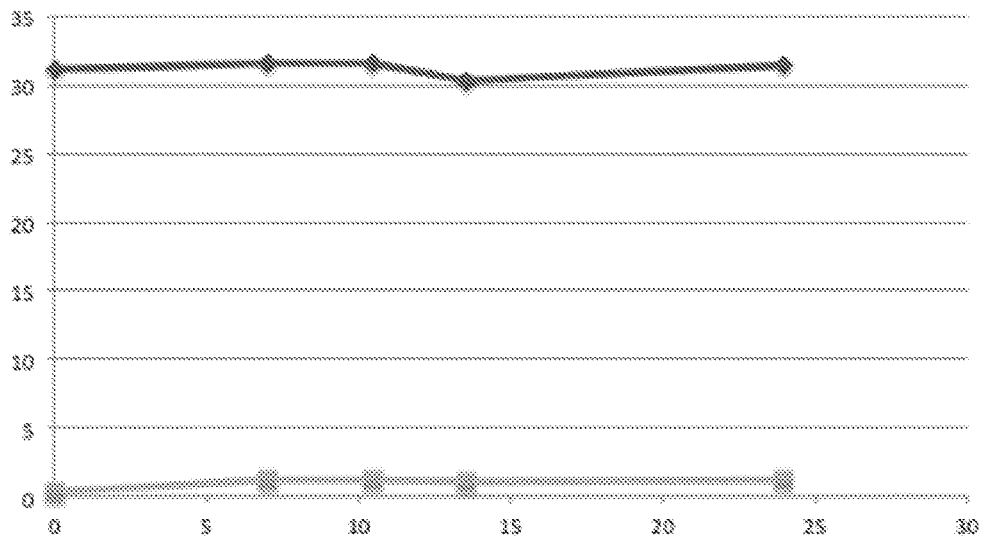
In FIG. 1, it is noted the consumption of xylose and ethanol production under anaerobic conditions by the microorganism described in the present invention after the process of genetic manipulation for insertion of genes of the pentose phosphate route and genetically modified gene of xylose isomerase, SEQ ID NO: 1, and before the evolution process. In the vertical axis, the concentration is described in grams per liter (g/L) and in the horizontal axis, the time in hours. The concentration of xylose is indicated by (♦), while the concentration of ethanol by time, is represented by (■).

It is one of the objects of the present invention an expression cassette for transforming eukaryotic cell comprising:
a) at least one nucleotide sequence selected from the group consisting of: xylose isomerase (SEQ ID NO: 1), transaldolase (SEQ ID NO: 5), ribose 5-phosphate isomerase (SEQ ID NO: 7), xylulokinase (SEQ ID NO: 9), transcetolase (SEQ ID NO: 11) and ribose 5-phosphate epimerase (SEQ ID NO: 12);
b) at least one promoter nucleotide sequence selected from the group consisting of: promoter glyceraldehyde 3-phosphate dehydrogenase (SEQ ID NO: 2), promoter 3-phosphate kinase (SEQ ID NO: 6), promoter of alcohol dehydrogenase 1 enzyme (SEQ ID NO: 8);

c) at least one terminator nucleotide sequence selected from the group consisting of: terminator glyceraldehyde 3-phosphate dehydrogenase (SEQ ID NO: 3), terminator of alcohol dehydrogenase (SEQ ID NO: 10), terminator 3-phosphate kinase (SEQ ID NO: 13);

and wherein the nucleotide sequence defined in a) is functionally linked to the promoter nucleotide sequence defined in b) and to the terminator nucleotide sequence defined in c), being heterologous any one of said sequences.

In one embodiment, the expression cassette is selected from the group consisting of:

a) expression cassette which comprises gene encoding xylose isomerase of sequence SEQ ID NO: 1, TDH1 promoter of nucleotide sequence SEQ ID NO: 2, and TDH1 terminator of nucleotide sequence SEQ ID NO: 3;

b) expression cassette which comprises ADH1 promoter represented by the sequence SEQ ID NO: 8, XKS1 gene represented by the sequence SEQ ID NO: 9 and ADH1 terminator represented by the sequence SEQ ID NO: 10;

c) expression cassette which comprises TDH1 promoter of nucleotide sequence SEQ ID NO: 2, TAL1 gene of sequence SEQ ID NO: 5, TDH1 terminator gene of sequence SEQ ID NO: 3, followed by PGK1 promoter of sequence SEQ ID NO: 6, by RKI1 gene (SEQ ID NO: 7) and by terminator of nucleotide sequence SEQ ID NO: 13;

d) expression cassette which comprises TDH1 promoter of sequence SEQ ID NO: 02, TKL1 gene of sequence SEQ ID NO: 11, encoding gene of Ribose 5-Phosphate Epimerase (SEQ ID NO: 7), TDH1 terminator of sequence SEQ ID NO: 3, followed by PGK1 promoter of sequence SEQ ID NO: 6, RPE1 gene of sequence SEQ ID NO: 12 and PGK1 terminator of sequence SEQ ID NO: 13; and combinations of at least two expression cassettes as described above;

and wherein said expression cassette(s) is/are functional in the eukaryotic cell(s).

In one embodiment, said promoter(s) is/are constitutive or naturally inducible.

It is another object of the present invention, the process for transforming the eukaryotic cell comprising the introduction, in the cell to be transformed, of at least one expression cassette as revealed by the present invention. In one embodiment, the introduction is in the genome of the cell to be transformed.

In one embodiment, the expression cassette further comprises the inactivation or deletion of the gene GRE3 (SEQ ID NO: 14) in the genome of said eukaryotic cell.

It is another object of the present invention, a genetically modified microorganism comprising at least one expression cassette as defined in the present patent application.

In one embodiment, one or more of said expression cassettes are present in the region of 5 thousand first base pairs counted from centromere both in upstream and downstream direction, which may be even just upstream, just downstream or both simultaneously.

In one embodiment, the promoter sequences, encoding sequences and terminator sequences of expression cassettes are stable in the microorganism genome and/or are present in at least 5 copies in the microorganism genome.

In one embodiment, the GRE3 gene (SEQ ID NO: 14) is inactivated or deleted in/from its genome.

In one embodiment, the microorganism is yeast of genus selected from the group consisting of: *Saccharomyces, Scheffersomyces, Spathaspora, Pichia, Candida, Kluyveromyces, Schizosaccharomyces, Brettanomyces, Hansenula* and *Yarrowia*.

In one embodiment, the microorganism is *Saccharomyces cerevisiae* DSM28739.

It is another object of the present invention the genetically modified microorganism *Saccharomyces cerevisiae* DSM28739.

It is another object of the present invention the production process of biofuels and/or biochemicals comprising a step of microorganism cultivation as defined in the present invention.

In one embodiment, the process yield is of at least 0.45 grams of ethanol produced by gram of xylose consumed by microorganism in synthetic medium which comprises xylose as source of carbon.

In one embodiment, the volumetric productivity is of at least 0.67 grams of ethanol produced by liter each hour, when in synthetic medium which comprises xylose as source of carbon.

In one embodiment, the microorganism is the microorganism *Saccharomyces cerevisiae* DSM28739.

It is another object of the present invention a biofuel obtained by the production process of biofuels and/or biochemicals comprising a step of microorganism cultivation as defined in the present invention.

It is another object of the present invention a biochemical obtained by the production process of biofuels and/or biochemicals comprising a step of microorganism cultivation as defined in the present invention.

The present invention describes, among other objects, a genetically modified microorganism with efficient fermentative performance in the conversion of sugars contained in the vegetal biomass, in biofuels and/or biochemicals, when compared to its version without the genetic modifications described in the present document.

More specifically, the genetically modified microorganism described in the present invention refers to a genetically transformed eukaryotic cell, preferably yeast or filamentous fungi.

In this invention, yeasts are considered as any subject from the group Eumycotina, that is, true fungi, which grow unicellularly and which make preferably anaerobic fermentation, such as, for example, *Saccharomyces, Scheffersomyces, Spathaspora, Pichia, Candida, Kluyveromyces, Schizosaccharomyces, Brettanomyces, Hansenula* and *Yarrowia*.

Filamentous fungi, in turn, are those characterized by having vegetative mycelium and growing from the hyphal elongation, in addition to performing aerobic respiration, such as, for example, *Aspergillus, Penicillium, Fusarium, Trichoderma, Moniliophthora* and *Acremonium*.

Even more specifically, the present invention describes a genetically modified microorganism, preferably yeast of *Saccharomyces* genus.

The described microorganism presents efficient performance in the conversion of sugars present in the vegetal biomass, preferably lignocellulosic material, in biochemicals or biofuels. One embodiment of the invention describes a microorganism of *Saccharomyces cerevisiae* species more efficient in the conversion of pentoses present in the lignocellulosic material in alcohols and/or biochemicals, such as, for example, succinic acid, malic acid, 1,3-propanediol, 1,2-propanediol, butanol, isobutanol, biodiesel, 1,4-butanediol, 2,3-butanediol, PHB—poly(butyrate hydroxide), however, without being restricted to these, when compared to its version without the genetic modifications contained in the present document.

Pentose preferably used by microorganism for conversion in alcohols and/or biochemicals above indicated is xylose, without however be restricted to it.

In the present invention, references are made to several gene sequences, all listed in the Sequence Listing section. For brief reference and ease of understanding, its respective functions or genes are indicated in the following table 1.

TABLE 1

Sequences referred to in the present invention and respective genes/functions.

| Gene/function | Sequence |
| --- | --- |
| Xylose Isomerase | SEQ ID NO: 1 |
| Promoter Glyceraldehyde 3-Phosphate Dehydrogenase, isoenzyme 1 (TDH1) | SEQ ID NO: 2 |
| Terminator Glyceraldehyde 3-Phosphate Dehydrogenase, isoenzyme 1 (TDH1) | SEQ ID NO: 3 |
| URA3 e loxp | SEQ ID NO: 4 |
| Transaldolase (TAL1) | SEQ ID NO: 5 |
| Promoter 3-Phosphate Kinase (PGK1) | SEQ ID NO: 6 |
| Ribose 5-Phosphate Isomerase (RKI1) | SEQ ID NO: 7 |
| Promoter of Alcohol Dehydrogenase 1 enzyme (ADH1) | SEQ ID NO: 8 |
| Xylulokinase (XKS1) | SEQ ID NO: 9 |
| Terminator of Alcohol Dehydrogenase (ADH1) | SEQ ID NO: 10 |
| Transcetolase (TKL1) | SEQ ID NO: 11 |
| Ribose 5-Phosphate Epimerase (RPE1) | SEQ ID NO: 12 |
| Terminator 3-Phosphate Kinase (PGK1) | SEQ ID NO: 13 |
| Aldose Reductase (GRE3) | SEQ ID NO: 14 |
| Recombinase CRE | SEQ ID NO: 15 |
| LTR of retrotransposon Ty1 | SEQ ID NO: 16 |
| LEU2 (ORF + promoter and terminator) | SEQ ID NO: 17 |

The sequence of nucleotides represented by SEQ ID NO: 1, which encodes a peptide with xylose isomerase feature, when inserted in eukaryotic cell, provides an expression of an enzyme favoring the isomerization of xylose into xylulose.

The microorganism described in the present invention is genetically modified by the introduction of sequence of nucleotides encoding a peptide with xylose isomerase function. This of nucleotides, originally described in *Orpinomyces* sp. (XI, EC 5.3.1.5), was manually optimized by the inventors for the codons preferably used by *Saccharomyces cerevisiae*. The optimized sequence of xylose isomerase used in the present invention is, however, not natural and different from natural sequences of xylose isomerase already described in public banks and is represented in SEQ ID NO: 1.

After optimization of the sequence represented in SEQ ID NO: 1, the CAI (Codon Adaptation Index), index which determines the possibility of high levels of protein expression, was 0.79 to 0.91, indicating the obtaining of an efficient expression of this protein in *S. cerevisiae*. The CAI index is the geometric mean of relative values of adaptation and for its calculation, non-synonymous codons are excluded and, in some cases, also those of termination. The values vary between 0 and 1, and larger ones indicate higher proportion of the most abundant codons [Nucleic Acids Research 15: 1281-1295].

Thus, the present invention also describes an expression cassette which comprises the sequence of nucleotides represented in SEQ ID NO: 1, encoding the peptide of xylose isomerase type and that, optionally, can be inserted into eukaryotic cell for the expression of said isomerase in its active form. In the present document, the genes are inserted into microorganism through the homologous recombination, thus starting to integrate its genome. The expression cassette of the invention is characterized in that it comprises: —a sequence (SEQ ID NO: 1) of nucleotides encoding a peptide with xylose isomerase function; —at least one promoter for said encoding nucleotide sequence; and—one nucleotide sequence selected from: one terminator nucleotide sequence of transcription; one selection marker; one or more encoding nucleotide sequence(s) of other enzymes; combinations thereof or one plasmid comprising such sequences, being heterologous at least one of nucleotide sequences defined above. One or more expression cassettes may be used in the transformation of eukaryotic cells according to the invention.

Optionally, the expression cassette of the invention also comprises sequences selected from the group which comprises the encoding sequences of Xylulokinase enzymes (SEQ ID NO: 9), Transaldolase (SEQ NO ID:5), Transcetolase (SEQ ID NO: 11), Ribose 5-Phosphate Isomerase (SEQ ID NO: 7) and/or Ribose 5-Phosphate Epimerase (SEQ ID NO: 12).

In one embodiment, the eukaryotic/microorganism host cell is yeast of the *Saccharomyces cerevisiae* species, however, it should be noted that any eukaryotic cell may be transformed with one or more expression cassettes of the invention, which comprises the sequence of nucleotides described in SEQ ID NO: 1.

Therefore, the present invention provides a eukaryotic cell, yeasts or filamentous fungi, preferably yeast of the *Saccharomyces cerevisiae* species, transformed with the sequence of nucleotides described in SEQ ID NO: 1, which can be presented in a single copy or, preferably, multiple copies of this sequence of nucleotides can be inserted into the genome.

In one embodiment, the genetically modified host cell further comprises genes of the pentose phosphate route, so that the insertion of SEQ ID NO: 1, which encodes xylose isomerase, favors the isomerization of xylose in xylulose. However, additionally to the insertion of SEQ ID NO: 1 in the host cell, the present invention describes genetic modifications in the same cell aiming to favor the metabolic flow through the routes of pentose phosphate, not being such modifications, however, a restrictive factor for transforming the host cell with the sequence of nucleotides represented in SEQ ID NO: 1.

For increased flow of pentose phosphate route in the host cell, genes encoding the enzymes Xylulokinase are inserted (XKS1, EC 2.7.1.17), whose sequence of nucleotides is represented in this document by SEQ ID NO: 9, Transaldolase (TAL1, EC 2.2.1.2), represented by the sequence SEQ NO ID:5, Transcetolase (TKL1, EC 2.2.1.1), whose sequence of nucleotides is represented by SEQ ID NO: 11, Ribose 5-Phosphate Isomerase (RKI1, EC 5.3.1.6), whose sequence of nucleotides is represented by SEQ ID NO: 7; and Ribose 5-Phosphate Epimerase (RPE1, EC 5.1.3.1), whose sequence of nucleotides is represented by SEQ ID NO: 12.

Among the enzymes presented, and that constitute the pentose-phosphate route, as well as the xylose isomerase represented by SEQ ID NO: 1, at least one the genes encoding them must present itself overexpressed and, preferably, linked to the constitutive promoters, that is, those that are constantly expressed, regardless of the condition to which the cell is subjected, or naturally inducible promoters. In the present document, promoters are defined as a regulatory region, located in the 5' region of the under its action and responsible for the start of transcription, while terminators are defined as a sequence which determines the final of the gene during the transcription process.

The overexpression of the genes encoding these enzymes can be due to the increased number of copies of the sequence of nucleotides encoding them, expression of episomal genes present in vector that can be inserted in the eukaryotic host cell, through the use of heterologous promoters to that sequence in which it is operably linked, or even homologous of the cell where they were inserted, or as endogenous in the host cell, as long as they are able to produce a stable state of transcription higher than would be achieved by the cell in its version without the present genetic modifications, in the situations wherein the sources of carbon as glucose and xylose are available in the environment. These promoters may be constitutive or naturally inducible.

In one embodiment, the present invention describes host cell comprising an expression cassette containing endogenous genes of enzymes of the non-oxidative phase of the pentoses phosphate route, which are, preferably, constructed using strong and constitutive promoters of the cell in which they will be inserted. Specifically, the present invention describes four embodiments of integrative expression cassettes, which were constructed using high expression and constitutive promoters of Saccharomyces cerevisiae, and stably integrated to the host cell genome.

One of the described cassettes contains the gene encoding xylose isomerase, SEQ ID NO: 1. In this cassette, a copy of SEQ ID NO: 1 is inserted into the flanked host cell, preferably, by the promoter and terminator region of the gene Glyceraldehyde 3-Phosphate Dehydrogenase, isoenzyme 1 (TDH1). Thus, briefly, the cassette which contains the gene encoding xylose isomerase and that was inserted into the host cell genome is formed by the promoter TDH1, whose sequence of nucleotides is represented by SEQ ID NO: 2, gene XI (SEQ ID NO: 1) and terminator TDH1, whose sequence of nucleotides is represented by SEQ ID NO: 3.

A second cassette described in the present invention, contains gene encoding the enzyme Xylulokinase (SEQ ID NO: 9). The present description indicates that the cassette is, preferably, constructed using gene promoter and terminator of the gene encoding alcohol dehydrogenase enzyme (ADH1). Thus, it is described that the cassette which contains the encoding gene of Xylulokinase is constructed by the promoter ADH1, represented by SEQ ID NO: 8, XKS1 gene (SEQ ID NO: 9) and terminator ADH1, represented by SEQ ID NO: 10.

One more cassette described in the present invention contains encoding genes of Transaldolase (SEQ NO ID:5) and Ribose 5-Phosphate Isomerase (SEQ ID NO: 7). This cassette is constructed, preferably using promoters and terminators of the gene encoding enzyme Glyceraldehyde 3-Phosphate Dehydrogenase, isoenzyme 1 (TDH1) to flank the gene Transaldolase and promoters and terminators of the enzyme 3-phosphoglycerate Kinase (PGK1) to flank the gene of Ribose 5-Phosphate Isomerase. Thus, briefly, the expression cassette is constructed, preferably, of promoter TDH1 (SEQ ID NO: 2), gene TAL1 (SEQ ID NO: 5) and terminator TDH1 (SEQ ID NO: 3), followed by promoter PGK1, whose sequence of nucleotides is represented by SEQ ID NO: 6, gene RKI1 (SEQ ID NO: 7) and terminator, whose sequence of nucleotides is represented by SEQ ID NO: 13.

The last cassette described in the present invention contains encoding genes of Transcetolase (SEQ ID NO: 11) and Ribose 5-Phosphate Epimerase (SEQ ID NO: 7), preferably, with associated function to the promoters and terminators of the genes Glyceraldehyde 3-Phosphate Dehydrogenase, isoenzyme 1 (TDH1), flanking the gene of Transcetolase and promoter and terminator of the gene encoding the enzyme 3-phosphoglycerate Kinase (PGK1). Thus, briefly, the expression cassette which was inserted into the host cell genome and contains the genes of Transcetolase and Ribose 5-Phosphate Epimerase, is constructed preferably by promoter TDH1 (SEQ ID NO: 2), gene TKL1 (SEQ ID NO: 11) and terminator TDH1 (SEQ ID NO: 3), followed by promoter PGK1 (SEQ ID NO: 6), gene RPE1 (SEQ ID NO: 12) and terminator PGK1 (SEQ ID NO: 13).

All expression cassettes with the genes of metabolic route of pentose phosphate favoring the consumption of xylose are inserted into the region of the target chromosome located between the centromere and the first gene adjacent to it, preferably in the region of 5 thousand first base pairs counted from the centromere both in upstream and downstream direction, and may even be just upstream, just downstream or both simultaneously.

The upstream direction is considered that located previously to the start point of the transcription unit of a DNA sequence, which starts in the promoter and ends in the terminator. In turn, downstream is considered the region located after the start point of the transcription unit of a DNA sequence.

In addition to the insertion of expression cassettes, the present invention also describes the deletion or inactivation of the GRE3 gene, which encodes aldose reductase and is represented in SEQ ID NO: 14. The production of xylitol reduces the total yield of ethanol which can be obtained. In addition, xylitol is an inhibitor of the action of xylose isomerase enzyme.

When performed in Saccharomyces cerevisiae, the above-mentioned genetic modifications favor the flow of the non-oxidative part of the pentose-phosphate route.

Then, the Example 4, shows that the simple insertion of the gene favoring the metabolic flow by the pentose phosphate route, as well as the gene encoding peptide of xylose isomerase type in the host cell, does not guarantee efficient consumption of pentoses present in the medium.

Therefore, the present invention describes the stable integration and high number of copies of cassette expressing XI (SEQ ID N:1) in the host cell genome. In the present document, it is considered high number of copies the insertion of, at least, 5 copies of gene in question, being preferential the insertion of at least 20 copies.

The present document describes, however, and eukaryotic cell, preferably microorganism of the Saccharomyces cerevisiae species, genetically modified containing in its genome at least one of the genes of enzymes needed to favor the non-oxidative part of the pentose phosphate route, inserted preferably in high number of copies and in the region between the centromere and its first adjacent gene. By having all metabolic route needed to convert xylose, in aerobic conditions, the line is able to consume the xylose present in the cultivation medium, but in anaerobic conditions, the consumption is very slow.

In the present invention, it is further described a process of directed evolution from which is obtained a microorganism with greater capacity of xylose consumption in anaerobic conditions and, thereafter, higher growth rate and higher production of biochemicals compounds and biofuels by time frame, when compared with the microorganism that was not subjected to said process. In said process, a microorganism of the Saccharomyces cerevisiae species was subjected to evolutionary pressures which consisted of progressive increases of xylose concentration as the only source of carbon, in order to select microorganisms with random mutations which favor higher consumption of xylose in anaerobic conditions and, accordingly, higher growth rate and higher production of biochemicals compounds and biofuels, preferably ethanol. Example 4 shows comparative results between the microorganism resulting from this process and the microorganism before the process of directed evolution. The genetically modified microorganism described in the present invention presents differentially the features of being non-flocculating, presenting high yield of ethanol, low formation of glycerol and xylitol, high viability, high growth rate, non-production of foam, in addition to efficient capacity of resistance to the stressful process of industrial fermentation. This microorganism is filed in the German Collection of Microorganisms and Cell Culture-Leibniz-lnstitut DSMZ, under number DSM28739.

The microorganism DSM28739 described in the present invention shows features of industrial interest such as: being a non-flocculating strain, presenting high yield of ethanol, low formation of glycerol and xylitol, high viability, high growth rate, non-production of foam, among others.

Further, the present invention describes a production process of biofuels and biochemicals from vegetal biomass, preferably a lignocellulosic portion of the vegetal biomass. The process described in the present invention uses the microorganism of the invention for producing biofuels and/or biochemicals.

In one embodiment, the process consists in the following steps:
put the microorganism DSM28739 in contact with lignocellulosic material; and
optionally, make the posterior collection of the generated compound.

In another embodiment, said lignocellulosic material is obtained by pre-treatment of lignocellulosic vegetal biomass, followed by hydrolysis.

The process of the invention provides the production of biofuels which comprise alcohols predominantly, especially ethanol. The process of the invention provides the production of biochemicals selected from the group which comprises, but is not limited to: succinic acid, malic acid, 1,3-propanediol, 1,2-propanediol, butanol, isobutanol, biodiesel, 1,4-butanediol, 2,3-butanediol and/or PHB—poly (butyrate hydroxide).

The present invention describes, finally, biofuels, preferably ethanol, and biochemicals produced by the process using the microorganism of the invention, such as DSM28739.

EXAMPLES

Example 1

Construction of Cassettes for the Expression and Insertion Thereof into the Genome For constructing each one of the cassettes containing genes of non-oxidative phase of the pentoses phosphate route, including gene of Xylose Isomerase, each one of genes was amplified by PCR of the S. cerevisiae genome and cloned in integrative expression cassettes.

Adjacent to the terminator of each cassette, the flanked URA3 gene was cloned by two loxP regions in the same orientation, allowing this region to be removed by the expression of Cre recombinase and the URA3 auxotrophic marker to be used in all expression cassettes with the described genes.

With regard to the construction of the expression cassette which contains gene encoding xylose isomerase, in addition to the above-mentioned construction, in the cassette ends, 126 pb were cloned from each side with homology to a region close to the chromosome five of Saccharomyces cerevisiae, allowing the integration through homologous recombination in this region.

For the construction of expression cassette with gene encoding xylulokinase, for example, this gene was amplified by PCR of the S. cerevisiae genome and it was cloned adjacent to the promoter and terminator of the gene encoding Alcohol dehydrogenase (ADH1). After the terminator, the flanker URA3 gene was inserted by two loxP regions in the same orientation. In the cassette ends, homology regions close to the centromere two and eight of S. cerevisiae were cloned. Two transformations were carried out to insert the cassettes expressing the gene XKS1 to 288 pb of the centromere two and the 228 pb of centromere eight. In this was, in addition to the endogenous copy, the transformant has two more copies of the gene XKS1 under the action of a high expression constitutive promoter.

In relation to the expression cassette which contains encoding genes of Transaldolase (TAL1) and Ribose 5-Phosphate Isomerase (RKI1), for example, these genes were cloned under the action of promoters and terminators of the genes Glyceraldehyde 3-Phosphate Dehydrogenase, isoenzyme 1 (TDH1) and 3-phosphoglycerate Kinase (PGK1), respectively, separated by flanked URA3 marker by the IoxP sites, and properly inserted into the host cell chromosome.

In relation to the expression cassette which contains encoding genes of Transcetolase (TKL1) and Ribose 5-Phosphate Epimerase (RPE1), for example, these genes were cloned under the action of promoters and terminators of the genes Glyceraldehyde 3-Phosphate Dehydrogenase, isoenzyme 1 (TDH1) and 3-phosphoglycerate Kinase (PGK1), respectively, separated by flanked URA3 marker by the IoxP sites, and properly inserted into the host cell chromosome.

The transformation of the host cell with each one of the cassettes containing genes of the non-oxidative phase of the pentose phosphate route followed the Gietz and Schiestl protocol [*Nature Protocols* 2, 31-34; 2007], through lithium acetate, and each one of the genes, flanked by strong and constitutive promoters and terminators of *Saccharomyces cerevisiae*, was stably integrated to the host cell chromosome. The correct integration was confirmed by PCR. After confirmation, the URA3 region was excised from genome by transient expression of Cre recombinase, leaving only one IoxP site on the place, after the terminator of inserted gene.

In the cassette ends of Xylose Isomerase, 126 pb were cloned from each side with homology to a region next to the chromosome five of *Saccharomyces cerevisiae*, allowing the integration through homologous recombination in this region.

Example 2

Insertion of Cassette of Xylose Isomerase into the Genome in High Number of Copies To guarantee the stable integration and high number of copies in the host cell, the cassette expressing the Xylose Isomerase represented by SEQ ID NO: 1 was modified with the inclusion, in the cassette ends, of delta elements of retrotransposon Ty1 (element present in high number of copies in to S. cerevisiae genome).

The URA3 marker flanked by the IoxP regions is replaced in this plasmid by the LEU2 marker. Previously, the LEU2 gene is deleted in a step of genetic manipulation. In this step, the URA3 gene, flanked by the IoxP regions adjacent to the homology regions to the promoter and terminator of LEU2 is integrated, resulting in the deletion of this gene. Then, the XI cassette is inserted, flanked by the Ty1elements and using the LEU2 auxotrophic marker for selecting transformants.

Example 3

Deletion of Gre3 Gene

The deletion of GRE3 gene, which encodes aldose reductase and is represented in SEQ ID NO: 14, was carried out in two steps through the genetic manipulation, aiming to reduce the production of xylitol from xylose. In the first step, the URA3 gene, flanked by the IoxP regions adjacent to the homology regions to the promoter and terminator of the GRE3 gene was integrated, resulting in the deletion of this region. In the second step, after the deletion confirmed, the URA3 marker was removed by transient expression of Cre recombinase.

Example 4

Adaptative Evolution and Consumption of Xylose

After being genetically manipulated with the insertion of all gene of the metabolic route necessary for converting xylose and before being subjected to adaptive evolution, the genetically modified microorganism, when in anaerobic conditions, consumed the xylose present in the cultivation medium slowly and with low generation of biofuel, in this case ethanol, as can be seen in FIG. 1.

Figure 2:
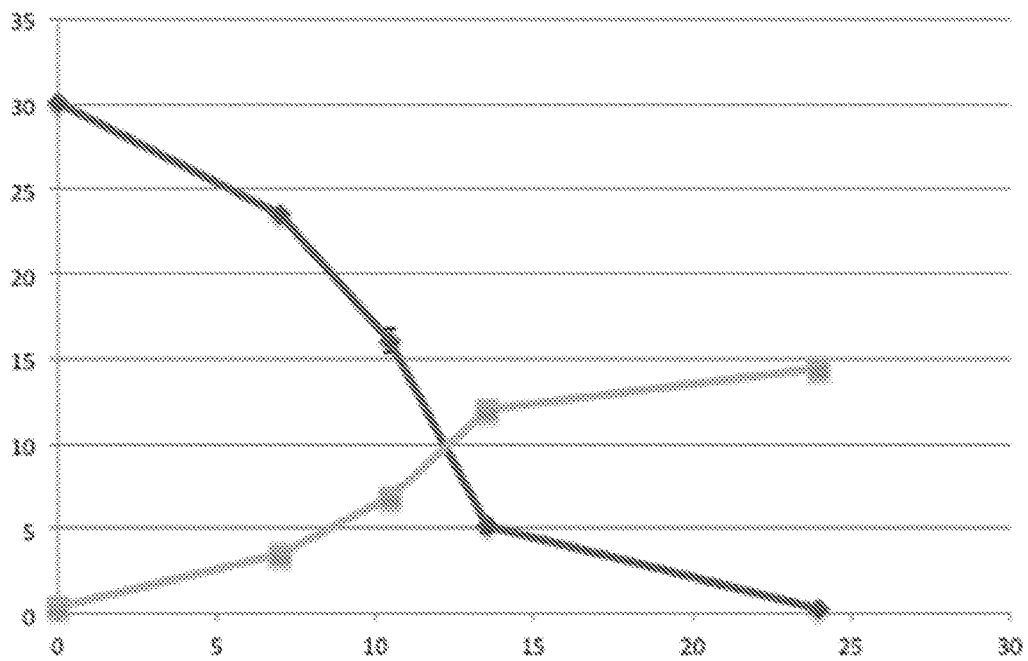
In FIG. 2, it is noted the consumption of xylose and ethanol production under anaerobic conditions by the microorganism described in the present invention after the process of genetic manipulation for insertion of genes of the pentose phosphate route and genetically modified gene of xylose isomerase, SEQ ID NO: 1, and after the evolution process. In the vertical axis, the concentration is described in g/L and in the horizontal axis, the time in hours. The concentration of xylose is indicated by (♦), while the concentration of ethanol by time is represented by (■).

Said microorganism was subjected to a process of evolutionary engineering which consisted of successive repetitions in medium containing 50 g/L of xylose under semi-anaerobic conditions. The inoculum was started with optical density (OD) of ~1.0. Due to a low initial growth, a low quantity of glucose was added to the medium in the first experiments (0.5%) aiming the culture to grow faster. After 48 hours of cultivation, an aliquot was transferred to a new flask with culture medium and the experiment was repeated. In the third transfer, it was not necessary the addition of glucose to the cultivation medium because of increased growth speed of the microorganism in xylose as the only source of carbon. 20 colonies of the mixture of evolved cells were isolated and analyzed. The microorganism DSM28739 was selected by its superior performance in terms of conversion capacity of xylose to ethanol, as can be seen in FIG. 2.

Example 5

Growth of Microorganism DSM28739 using Xylose as a Source of Carbon

Inoculum Preparation

A culture aliquot of the microorganism DSM28739 previously cryopreserved at −85° C. (in solution of glycerol 20%w/v) was reactivated in YEPD medium (20 g/L of glucose, 10 g of yeast extract and 20 g/l of peptone), during 6 hours in an Erlenmeyer of 100 mL containing 50 mL of YEPD medium, 20 g/L of glucose in an orbital shaker at 200 rpm and 30° C. Posteriorly, an aliquot of this culture was transferred to an Erlenmeyer of 500 ml containing 200 ml of YEPD medium 40 g/L of glucose.

The culture was initiated with an Optical Density (OD) equal to 0.1, when earned in 600nm of wavelength and incubated at 200 rpm and 30° C. during 16 hours. A volume of this culture was transferred to a conical bottom tube of 50 ml and centrifuged at 4000 rpm for 10 min. The pellet cells were washed 3 times in distilled water by centrifugation and resuspended in the appropriate culture medium for transference in the bioreactor (described below).

Cultivation in Bioreactor 600 mL of synthetic culture medium were prepared in a bottle of 1 L comprising xylose as one of the source of carbon, as the YEPX medium (20 g/L of xylose, 10 g/L of yeast extract and 20 g/L of bacteriological peptone). The bioreactor with work volume of 1 L was prepared with 500 mL of this culture medium.

The bioreactor was, then, sterilized in autoclave at 121° C. and 1 atm of pressure for 20 minutes. The remaining 100 mL were transferred to a bottle of 250 mL and also autoclaved. The source of carbon was dissolved in 100 mL of distilled and autoclaved water in a bottle of 250 mL. After autoclaving, the 100 mL containing the source of carbon were transferred to a bioreactor.

The inoculum was prepared from cells obtained by centrifugation of inoculum previously prepared with culture of the microorganism DSM28739. The cells were then resuspended in 100 mL of the medium without source of carbon and immediately inoculated in the bioreactor. The culture was initiated with OD=3.

During the cell growth, pH was kept in a pH range between 3 and 7, through addition of acids and/or bases. The temperature and the stirring speed were also kept constant in 30° C. and 200 rpm, respectively.

To guarantee the anaerobiosis state, before inoculation, the cultivation medium and the atmosphere of bioreactor with the nitrogen gas flow of 2 LN/min (normal liter per minute) during 10 minutes. Two samples of 1.5 mL were collected, approximately at each three hours. One sample was used to measure the OD, while the other was analyzed by high performance liquid chromatography (HPLC).

Quantification of Fermentation Products

The quantification of xylose, ethanol and glycerol was carried out by high performance liquid chromatography HPLC and using Alliance HT (Waters) chromatograph with refractive index detector (Waters 2414). The runs were performed using a column HPX-87H (BioRad) kept at 35° C., with 4 mM sulfuric acid as mobile phase and a flow of 0.6 mL/min.

Figure 3:
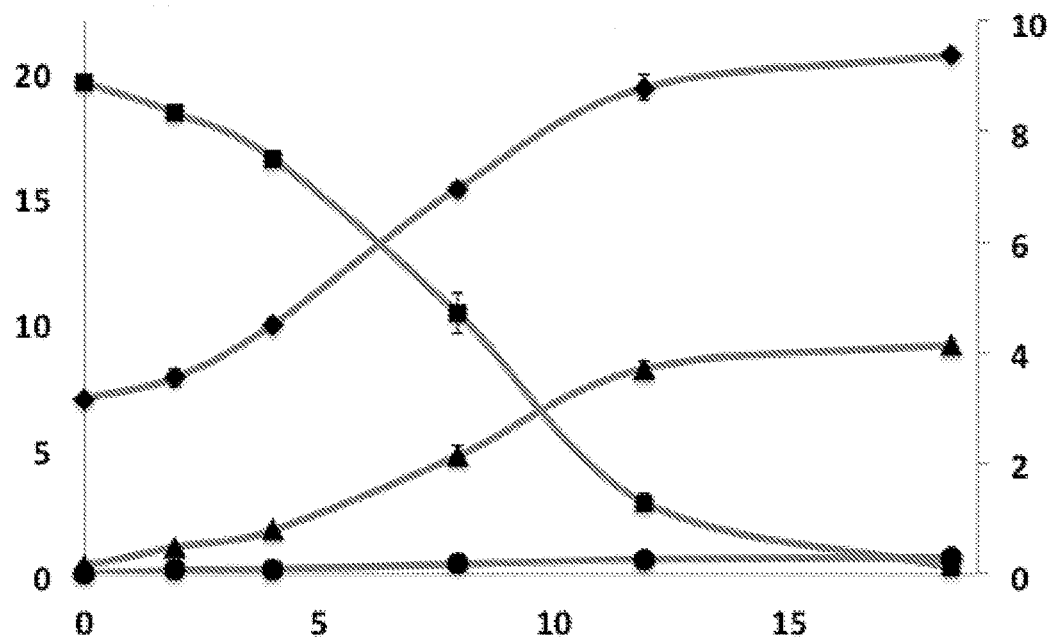
In FIG. 3, it is possible to observe the fermentation kinetics of the microorganism DSM28739 in synthetic medium comprising xylose as one of its source of carbon, as YEPX (20 g/L of xylose, 10 g/L of yeast extract and 20 g/L of bacteriological peptone). In the figure, the symbol (■) represents Xylose, (♦) represents cell growth expressed in optical density (OD), (▲) represents ethanol and (●) represents glycerol. In the presented figure, the vertical axis to the left represents the concentration (g/L) of each one of the analyzed compounds. The vertical axis to the right represents the Optical Density (OD) measured in 600 nm of absorbance. The horizontal axis, in turn, represents the fermentation time, expressed in hours.

Observing FIG. 3, it is possible to check that microorganism DSM28739 consumed 20 g/L of xylose in approximately 18 hours. The main fermentation product was the ethanol reaching approximately 9 g/L. Glycerol was also observed, but in low concentration. The glycerol production is observed in low concentration.

Table 2 shows the ethanol yield and volumetric productivity of microorganism DSM28739.

TABLE 2

Yield and volumetric productivity of microorganism DSM28739 in synthetic medium comprising xylose as one of the sources of carbon, such as the YEPX medium (20 g/L of xylose, 10 g/L of yeast extract and 20 g/L of bacteriological peptone).

| Line | Yield g/g (grams of ethanol produced by gram of consumed xylose) | Ethanol volumetric productivity of g/Lh (grams of ethanol produced per liter and per hour) |
|---|---|---|
| DSM28739 | 0.46 ± 0.01 | 0.69 ± 0.02 |

Example 6

Fermentation of Microorganism DSM28739 using Cane Straw Hydrolyzate.

Cultivation Medium

The cultivation medium was prepared using cane straw hydrolyzate containing between 20 to 60 g/L of xylose and/or 20 to 60 g/L of glucose. The hydrolyzate was supplemented with urea, in order to support the yeast growth.

Inoculum preparation

Culture aliquot of the microorganism DSM28739 previously cryopreserved at −85° C. (in solution of glycerol 20%w/v) was reactivated during 6 hours in an Erlenmeyer of 100 mL containing 50 mL of YEPD medium 20 g/L of glucose in an orbital shaker at 200 rpm and 30° C. Posteriorly, the aliquot of this culture was transferred to an Erlenmeyer of 500 ml containing 200 ml of YEPD medium 40 g/l of glucose. The culture was initiated with an OD=0.1 (optical density at 600 nm of wavelength), incubated at 200 rpm and 30° C. during 16 hours. A volume of this culture was transferred to a conical bottom tube of 50 ml and centrifuged at 4000 rpm for 10 min. The pellet cells were washed 3 times in distilled water by centrifugation and resuspended in the cultivation medium (hydrolyzed).

Cultivation in bioreactor 700 mL of cane straw hydrolizate were autoclaved in a bottle of 1 L. In the bioreactor with work volume of 1 L (previously autoclaved), 600 mL of the hydrolyzate were transferred and the remaining 100 mL were transferred to a bottle of 250 mL (previously autoclaved) for posterior resuspension of the inoculum. The inoculum was prepared from cells obtained by centrifugation in the previous item. The cells to the inoculum were resuspended in the 100 mL of the hydrolyzate and immediately inoculated in the bioreactor. The culture was initiated with an OD=1. During cell growth, pH was kept between 3 and 7 by automatic adding of aqueous solution of acids or bases, as, for example, KOH 3 mol/L or $H_2SO_4$ 1 mol/L. The temperature and the stirring speed were kept constant in 30° C. and 200 rpm respectively. To guarantee the anaerobiosis state, before inoculation, the cultivation medium and the atmosphere of the bioreactor were saturated with the nitrogen gas flow of 2 LN/min (normal liter per minute) during 10 minutes. Samples were collected in suitable intervals, immediately frozen in liquid nitrogen and kept frozen at −20° C. to posterior analysis by high performance liquid chromatography (HPLC).

Quantification of Fermentation Products

Figure 4:
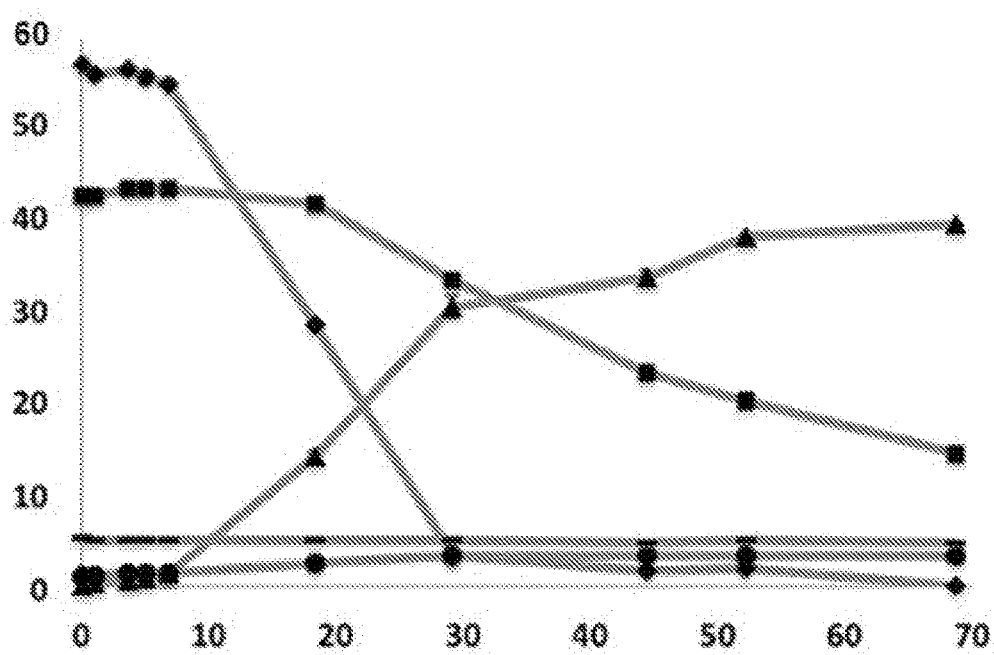
In FIG. 4, it is observed the fermentation kinetics of the microorganism DSM28739 in cane straw hydrolyzate, the concentration being represented in the vertical axis (g/L) and the time in hours in the horizontal axis. The concentration of xylose by time is represented by (■), glucose by (♦), the concentration of ethanol is represented by (▲), glycerol by (●) and acetic acid.

The quantification of xylose, ethanol and glycerol were carried out by high performance liquid chromatography HPLC and using the Alliance HT (Waters) chromatograph with refractive index detector (Waters 2414). The runs were performed using a column HPX-87H (BioRad) kept at 35° C., with 4 mM sulfuric acid as mobile phase and a flow of 0.6 mL/min. The fermentation kinetics of the microorganism DSM28739 in cane straw hydrolyzate, can be observed in FIG. 4.

The microorganism DSM28739 consumed glucose very fast in approximately 30 hours. After 70 hours, the major part of xylose was also consumed. The main fermentation product was ethanol, reaching approximately 37 g/L. The glycerol production is also observed in low concentration. The main inhibitor in the hydrolyzate, the acetic acid, was kept constant during all fermentation (around 5 g/L).

Table 3 shows the ethanol yield and the volumetric productivity of DSM28739 in cane straw hydrolyzate.

TABLE 3

Yield and volumetric productivity of microorganism DSM28739 in cane straw hydrolyzate.

| Line | Yield g/g (grams of ethanol produce per gram of consumed sugars) | Volumetric productivity of ethanol g/Lh (grams of ethanol produced per liter and per hour) |
|---|---|---|
| DSM28739 | 0.44 ± 0.009 | 0.64 ± 0.005 |

Example 7

Proof of Insertion of Cassettes into the Genetically Modified Microorganism DSM28739

The DNA of line DSM28739 was used as a model for the polymerase chain reaction using oligonucleotides yearning in an external region to the insertion of gene expression cassettes. For each reaction, it was used a pair of specific oligos for the external region of each inserted cassette.

After the experiment of polymerase chain reaction (PCR), an aliquot was applied to agarose gel 0.8%, stained with GelRed, and subjected to electrophoresis for separating the amplified fragments.

Figure 6:
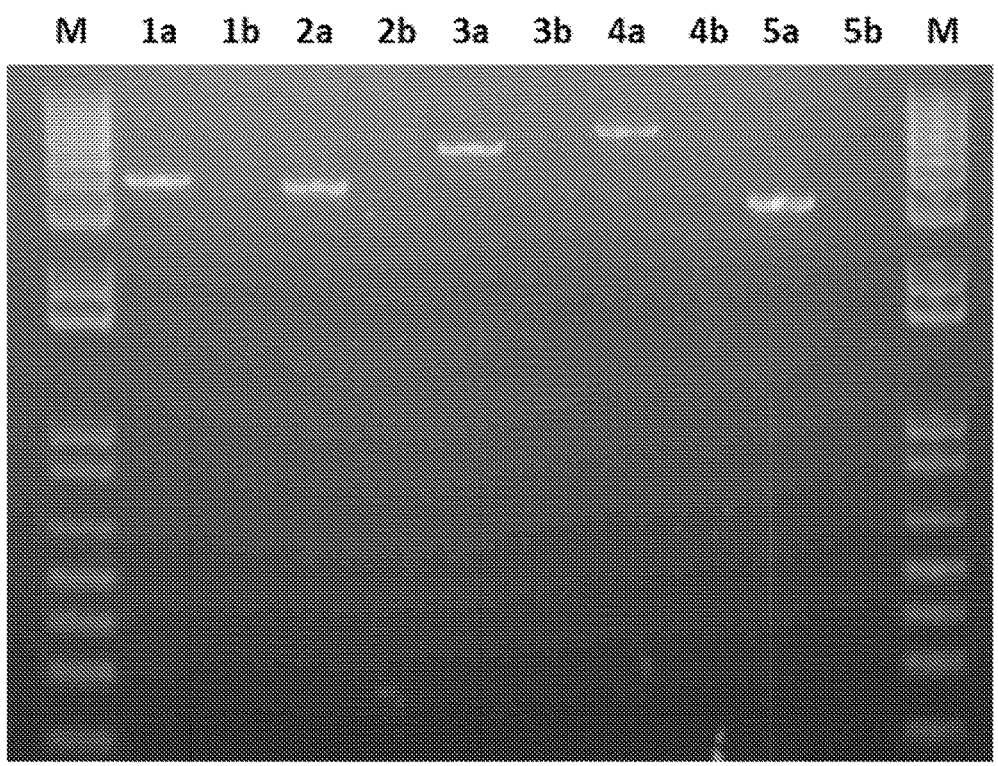
In FIG. 6, it is shown the electrophoresis gel obtained from amplification of external regions to the inserted cassette, confirming the integration to the yeasts. In the present figure, M represents the marker 1 kb ladder; 1a, the cassette of gene XKS1 inserted next to the centromere 2; 1b, the white of the reaction 1; 2a is the cassette of gene XKS1 inserted next to the centromere 8; 2b is the white of the reaction 2; 3a is the cassette of genes TAL1 and RKI1 inserted next to the centromere 12; 3b is the white of the reaction 3; 4a is the cassette of genes TKL1 and RKI1 inserted next to the centromere 13; 4b is the white of the reaction 4; 5a is the cassette of gene XI inserted next to the centromere 5; e 5b is the white of the reaction 5.
Figure 7:
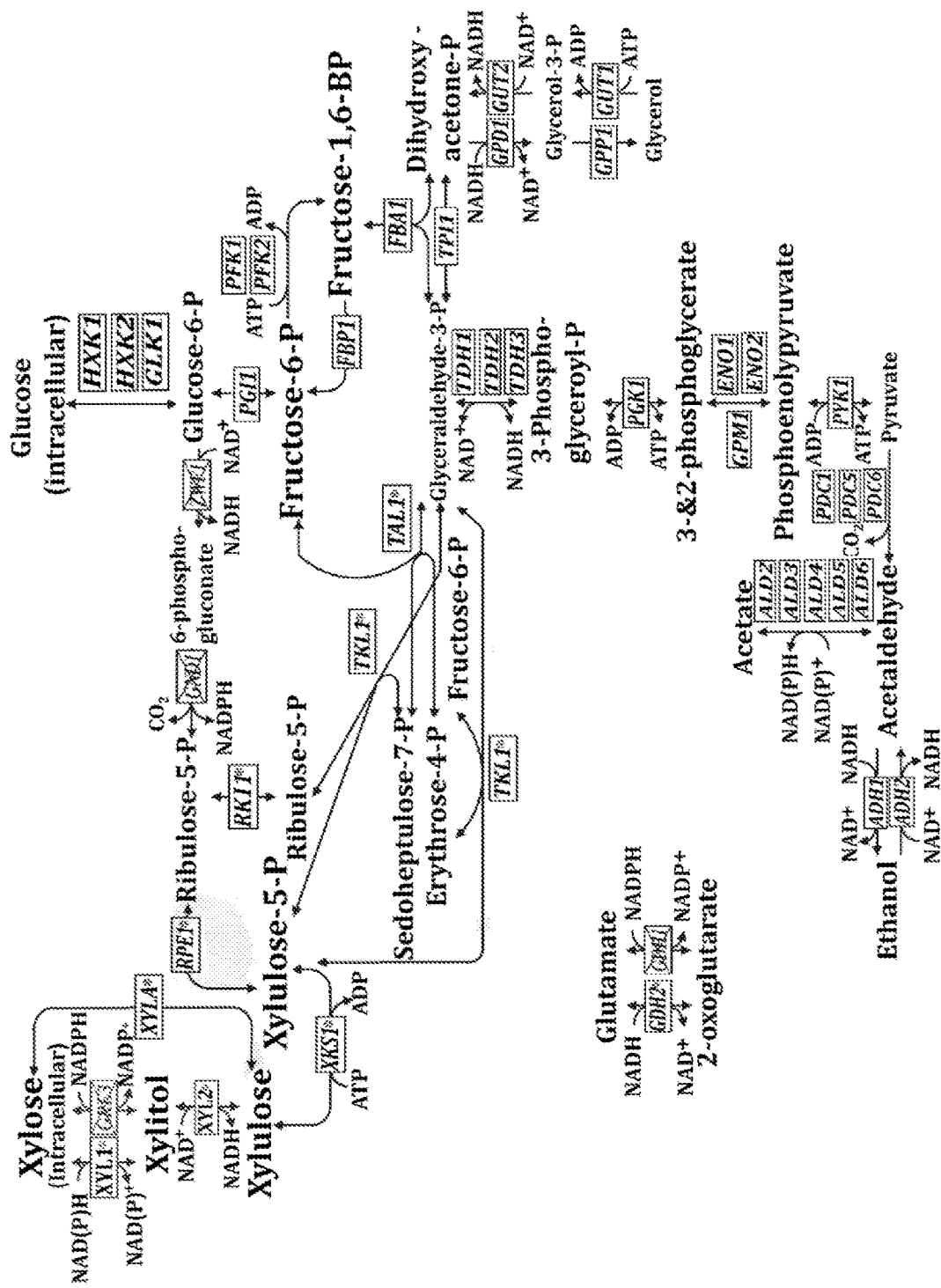
In FIG. 7, extracted from Matsushika et al., [Applied Microbiology and Biotechnology, 84:37-53, 2009], the modification made on *S. cerevisiae* can be viewed through the metabolic engineering for the xylose fermentation. The genes marked with asterisk were overexpressed; the crossed genes were deleted.

FIG. 6 shows the electrophoresis gel obtained from external reactions to the inserted cassettes, proving the integration to yeasts. In this figure, M represents the marker 1 kb ladder; 1a, is the cassette of gene XKS1 inserted next to the centromere 2; 1b, the white of the reaction 1; 2a is the cassette of gene XKS1 inserted next to the centromere 8; 2b is the white of the reaction 2; 3a is the cassette of genes TAL1 and RKI1 inserted next to the centromere 12; 3b is the white of the reaction 3; 4a is the cassette of genes TKL1 and RKI1 inserted next to the centromere 13; 4b is the white of the reaction 4; 5a is the cassette of gene XI inserted next to the centromere 5; and 5b is the white of the reaction 5.

Therefore, it is possible to observe in FIG. 6 that the cassettes were inserted correctly in the intended location. This result is observed due to the amplification of bands with similar size to the constructed cassette.

The invention claimed is:

1. A genetically modified microorganism, wherein the genetically modified organism is *Saccharomyces cerevisiae* DSM28739.

* * * * *

SEQUENCE LISTING

<160> NUMBER OF SEQ ID NOS: 17

<210> SEQ ID NO 1
<211> LENGTH: 1314
<212> TYPE: DNA
<213> ORGANISM: Artificial Sequence
<220> FEATURE:
<223> OTHER INFORMATION: Encoding sequence of peptide with feature of
      xylose isomerase

<400> SEQUENCE: 1

| | | |
|---|---|---|
| atgactaaag aatattttcc aactattggt aaaattagat tgaaggtaa agattctaag | 60 |
| aatccaatgg ccttccatta ctatgatgct gaaaaagaag tcatgggtaa gaaaatgaaa | 120 |
| gattggttaa gatttgccat ggcctggtgg catactttgt gcgccgatgg tgctgaccaa | 180 |
| ttcggtgttg gtactaagtc ttttccatgg aatgaaggta ctgacccaat tgctattgcc | 240 |
| aaacaaaagg ttgatgctgg ttttgaaatt atgaccaaat tgggtattga acattattgt | 300 |
| ttccacgatg ttgatttagt ttctgaaggt aattctattg aagaatatga atctaacttg | 360 |
| aaacaagttg ttgcttactt gaaacaaaag caacaagaaa ctggtattaa attattgtgg | 420 |
| tctactgcca atgttttttgg taatccaaga tatatgaacg gtgcctctac taatccagac | 480 |
| tttgatgtcg tcgccagagc tattgttcaa attaagaacg ccatggacgc cggtattgaa | 540 |
| ttgggtgctg aaaactacgt cttctggggt ggtagagaag ttatatgtc attgttaaac | 600 |
| actgaccaaa aaagagaaaa ggaacatatg gctactatgt tgactatggc tagagattac | 660 |
| gctagatcta aaggttttaa gggtactttc ttaattgaac caaaaccaat ggaaccaacc | 720 |
| aagcatcaat atgacgttga tactgaaact gttattggtt tcttgagagc tcacaattta | 780 |
| gacaaagact ttaaggtcaa cattgaagtt aatcacgcta ctttagctgg tcatactttc | 840 |
| gaacacgaat ggcctgtgc tgttgatgct ggtatgttag ttctattga tgctaacaga | 900 |
| ggtgactatc aaaatggttg ggacactgat caattcccaa ttgatcaata tgaattggtc | 960 |
| caagcttgga tggaaattat cagaggtgg ggttttgtta ctggtggtac caacttcgat | 1020 |
| gccaaaacta gaaggaactc taccgattta gaagatatta tcattgctca tatttctggt | 1080 |
| atggatgcca tggctagagc tttggaaaat gctgccaagt tattgcaaga atctccatat | 1140 |
| tgtaatatga aaaggaaag atacgcttct tttgactctg gtattggtaa agactttgaa | 1200 |
| gatggtaagt taactttgga acaagtttac gaatatggta aaaagaatgg tgaaccaaaa | 1260 |
| gttacttctg gtaagcaaga attatatgaa gctattgttg ccatgtacca ataa | 1314 |

<210> SEQ ID NO 2
<211> LENGTH: 742
<212> TYPE: DNA
<213> ORGANISM: Artificial Sequence
<220> FEATURE:
<223> OTHER INFORMATION: Glyceraldehyde 3-Phosphate Dehydrogenase
      Promoter, isoenzyme 1 (TDH1)

<400> SEQUENCE: 2

| | | |
|---|---|---|
| aatgtatatg ctcatttaca ctccatatca ccatatggag gataagttgg gttgagcttc | 60 |
| tgatccaatt tattctatcc attagttgct gatatgtccc accagccaac acttgatagt | 120 |
| atctactcgc cattcacttc cagcagcgcc agtagggttg ttgagcttag taaaaatgtg | 180 |
| cgcaccacaa gcctacatgt ctccacgtca catgaaacca caccgtgggg ccttgttgcg | 240 |
| ctaggaatag gatatgcgac gaagacgctt ctgcttagta accacaccac attttcaggg | 300 |
| ggtcgatctg cttgcttcct ttactgtcac gagcggccca taatcgcgct ttttttttaa | 360 |

```
aagacgcgag acagcaaaca ggaagctcgg gtttcaacct tcggagtggt cgcagatctg    420
gagactggat ctttacaata cagtaaggca agccaccatc tgcttcttag gtgcatgcga    480
cggtatccac gtgcagaaca acatagtctg aagaaggggg gaggagcatg ttcattctct    540
gtagcagtaa gagcttggtg ataatgacca aaactggagt ctcgaaatca tataaataga    600
caatatattt tcacacaatg agatttgtag tacagttcta ttctctctct tgcataaata    660
agaaattcat caagaacttg gtttgatatt tcaccaacac acacaaaaaa cagtacttca    720
ctaaatttac acacaaaaca aa                                             742
```

<210> SEQ ID NO 3
<211> LENGTH: 305
<212> TYPE: DNA
<213> ORGANISM: Artificial Sequence
<220> FEATURE:
<223> OTHER INFORMATION: Glyceraldehyde 3-Phosphate Dehydrogenase
      Terminator, isoenzyme 1 (TDH1)

<400> SEQUENCE: 3

```
ataaagcaat cttgatgagg ataatgattt tttttttgaat atacataaat actaccgttt     60
ttctgctaga ttttgtaaag acgtaaataa gtacatatta ctttttaagc caagacaaga    120
ttaagcatta actttaccct tttctcttct aagttttaac actagttatc actgttaaaa    180
aattatggcg agaacgtcgg cggttaaaat atattaccct gaatgtggtg aattgaagtt    240
cttggatggt ttaaagattt ttccttttttg ggaaataagt aaacaatata ttgctgcctt    300
tgcaa                                                                305
```

<210> SEQ ID NO 4
<211> LENGTH: 1349
<212> TYPE: DNA
<213> ORGANISM: Artificial Sequence
<220> FEATURE:
<223> OTHER INFORMATION: Encoding sequence of URA3 and loxp genes

<400> SEQUENCE: 4

```
cactataggg cgaattgggc ccgacgtcgc atgctcccgg ccgccatggc ggccgcggga     60
attcgatata acttcgtata gcatacatta tacgaagtta tggtccataa agcttttcaa    120
ttcatctttt ttttttttgt tcttttttttt gattccggtt tctttgaaat ttttttgatt    180
cggtaatctc cgagcagaag gaagaacgaa ggaaggagca cagacttaga ttggtatata    240
tacgcatatg tggtgttgaa gaaacatgaa attgcccagt attcttaacc caactgcaca    300
gaacaaaaac ctgcaggaaa cgaagataaa tcatgtcgaa agctacatat aaggaacgtg    360
ctgctactca tcctagtcct gttgctgcca agctatttaa tatcatgcac gaaaagcaaa    420
caaacttgtg tgcttcattg gatgttcgta ccaccaagga attactggag ttagttgaag    480
cattaggtcc caaaatttgt ttactaaaaa cacatgtgga tatcttgact gatttttcca    540
tggagggcac agttaagccg ctaaaggcat atccgccaa gtacaatttt ttactcttcg    600
aagacagaaa atttgctgac attggtaata cagtcaaatt gcagtactct gcgggtgtat    660
acagaatagc agaatgggca gacattacga atgcacacgg tgtggtgggc ccaggtattg    720
ttagcggttt gaagcaggcg gcggaagaag taacaaagga acctagaggc cttttgatgt    780
tagcagaatt gtcatgcaag ggctccctag ctactggaga atatactaag ggtactgttg    840
acattgcgaa gagcgacaaa gattttgtta tcggctttat tgctcaaaga gacatgggtg    900
gaagagatga aggttacgat tggttgatta tgacacccgg tgtgggttta gatgacaagg    960
```

```
gagacgcatt gggtcaacag tatagaaccg tggatgatgt ggtctctaca ggatctgaca    1020
ttattattgt tggaagagga ctatttgcaa agggaaggga tgctaaggta gagggtgaac    1080
gttacagaaa agcaggctgg gaagcatatt tgaagaatg cggccagcaa aactaaaaaa    1140
```
*(value as shown)*

```
gttacagaaa agcaggctgg gaagcatatt tgaagaatg cggccagcaa aactaaaaaa    1140
ctgtattata agtaaatgca tgtatactaa actcacaaat tagagcttca atttaattat    1200
atcagttatt acccgggaat ctcggtcgta atgatttcta taacttcgta tagcatacat    1260
tatacgaagt tatatcacta gtgaattcgc ggccgcctgc aggtcgacca tatgggagag    1320
ctcccaacgc gttggatgca tagcttgag                                     1349

<210> SEQ ID NO 5
<211> LENGTH: 1008
<212> TYPE: DNA
<213> ORGANISM: Artificial Sequence
<220> FEATURE:
<223> OTHER INFORMATION: Transaldolase (TAL1)

<400> SEQUENCE: 5
atgtctgaac cagctcaaaa gaaacaaaag gttgctaaca actctctaga acaattgaaa      60
gcctccggca ctgtcgttgt tgccgacact ggtgatttcg gctctattgc caagtttcaa     120
cctcaagact ccacaactaa cccatcattg atcttggctg ctgccaagca accaacttac     180
gccaagttga tcgatgttgc cgtggaatac ggtaagaagc atggtaagac caccgaagag     240
caagtcgaaa atgctgtgga cagattgtta gtcgaattcg gtaaggagat cttaaagatt     300
gttccaggca gagtctccac cgaagttgat gctagattgt cttttgacac tcaagctacc     360
attgaaaagg ctagacatat cattaaattg tttgaacaag aaggtgtctc caaggaaaga     420
gtccttatta aaattgcttc cacttgggaa ggtattcaag ctgccaaaga attggaagaa     480
aaggacggta tccactgtaa tttgactcta ttattctcct tcgttcaagc agttgcctgt     540
gccgaggccc aagttacttt gatttcccca tttgttggta gaattctaga ctggtacaaa     600
tccagcactg gtaaagatta aagggtgaa gccgacccag tgttatttc cgtcaagaaa     660
```

```
atctacaact actacaagaa gtacggttac aagactattg ttatgggtgc ttcttcaga     720 agcactgacg aaatcaaaaa cttggctggt gttgactatc taacaatttc tccagcttta     780
ttggacaagt tgatgaacag tactgaacct ttcccaagag tttggaccc tgtctccgct     840 aagaaggaag ccggcgacaa gatttcttac atcagcgacg aatctaaatt cagattcgac     900
ttgaatgaag acgctatggc cactgaaaaa ttgtccgaag gtatcagaaa attctctgcc     960
gatattgtta ctctattcga cttgattgaa agaaagtta ccgcttaa                 1008

<210> SEQ ID NO 6
<211> LENGTH: 873
<212> TYPE: DNA
<213> ORGANISM: Artificial Sequence
<220> FEATURE:
<223> OTHER INFORMATION: 3-Phosphate Kinase Promoter (PGK1)

<400> SEQUENCE: 6
tactgtaatt gcttttagtt gtgtattttt agtgtgcaag tttctgtaaa tcgattaatt      60
tttttttctt tcctcttttt attaacctta atttttattt tagattcctg acttcaactc     120
aagacgcaca gatattataa catctgcata ataggcattt gcaagaatta ctcgtgagta     180
aggaaagagt gaggaactat cgcatacctg catttaaaga tgccgatttg ggcgcgaatc     240
ctttattttg gcttcaccct catactatta tcagggccag aaaaaggaag tgtttccctc     300
```

```
cttcttgaat tgatgttacc ctcataaagc acgtggcctc ttatcgagaa agaaattacc      360
gtcgctcgtg atttgtttgc aaaaagaaca aaactgaaaa aacccagaca cgctcgactt      420
cctgtcttcc tattgattgc agcttccaat ttcgtcacac aacaaggtcc tagcgacggc      480
tcacaggttt tgtaacaagc aatcgaaggt tctggaatgg cgggaaaggg tttagtacca      540
catgctatga tgcccactgt gatctccaga gcaaagttcg ttcgatcgta ctgttactct      600
ctctctttca aacagaattg tccgaatcgt gtgacaacaa cagcctgttc tcacacactc      660
ttttcttcta accaagggggg tggtttagtt tagtagaacc tcgtgaaact tacatttaca     720
tatatataaa cttgcataaa ttggtcaatg caagaaatac atatttggtc ttttctaatt     780
cttagttttt caagttctta gatgctttct ttttctcttt tttacagatc atcaaggaag      840
taattatcta cttttttacaa caaatataaa aca                                  873

<210> SEQ ID NO 7
<211> LENGTH: 777
<212> TYPE: DNA
<213> ORGANISM: Artificial Sequence
<220> FEATURE:
<223> OTHER INFORMATION: Ribose 5-Phosphate Isomerase (RKI1)

<400> SEQUENCE: 7
atggctgccg gtgtcccaaa aattgatgcg ttagaatctt tgggtaatcc tttggaggat       60
gccaagagag ctgcagcata cagagcagtt gatgaaaatt taaatttga tgatcacaaa      120 ataattggaa ttggtagtgg tagcacagtg gtttatgttg ccgaaagaat tggacaatat      180
ttgcatgacc ctaaatttta tgaagtagcg tctaaattca tttgcattcc aacaggattc      240
caatcaagaa acttgatttt ggataacaag ttgcaattag gctccattga acagtatcct      300
cgcattgata tagcgtttga cggtgctgat gaagtggatg agaattaca attgattaaa      360 ggtggtggtg cttgtctatt tcaagaaaaa ttggttagta ctagtgctaa aaccttcatt      420
gtcgttgctg attcaagaaa aaagtcacca aacatttag gtaagaactg gaggcaaggt      480
gttcccattg aaattgtacc ttcctcatac gtgagggtca agaatgatct attagaacaa      540
ttgcatgctg aaaaagttga catcagacaa ggaggttctg ctaaagcagg tcctgttgta      600
actgacaata taacttcat tatcgatgcg gatttcggtg aaatttccga tccaagaaaa      660
ttgcatagag aaatcaaact gttagtgggc gtggtggaaa caggtttatt catcgacaac      720
gcttcaaaag cctacttcgg taattctgac ggtagtgttg aagttacgga aaagtga        777

<210> SEQ ID NO 8
<211> LENGTH: 702
<212> TYPE: DNA
<213> ORGANISM: Artificial Sequence
<220> FEATURE:
<223> OTHER INFORMATION: Promoter of Alcohol Dehydrogenase 1 enzyme
      (ADH1)

<400> SEQUENCE: 8
ttccgggtgt acaatatgga cttcctcttt tctggcaacc aaacccatac atcgggattc       60
ctataatacc ttcgttggtc tccctaacat gtaggtggcg gaggggagat atacaataga     120
acagatacca gacaagacat aatgggctaa acaagactac accatttaca ctgcctcatt     180
gatggtggta cataacgaac taatactgta gccctagact tgatagccat catcatatcg     240
aagtttcact accctttttc catttgccat ctattgaagt aataataggc gcatgcaact     300
tcttttcttt tttttttttt ctctctcccc cgttgttgtc tcaccatatc cgcaatgaca     360
```

| | | |
|---|---|---|
| aaaaaatgat ggaagacact aaaggaaaaa attaacgaca aagacagcac caacagatgt | 420 | |
| cgttgttcca gagctgatga ggggtatctc gaagcacacg aaacttttc cttccttcat | 480 | |
| tcacgcacac tactctctaa tgagcaacga tatacggcct tccttccagt tacttgaatt | 540 | |
| tgaaataaaa aaagtttgct gtcttgctat caagtataaa tagacctgca attattaatc | 600 | |
| ttttgtgttc tcgtcattgt tctcgttccc tttcttcctt gtttcttttt ctgcacaata | 660 | |
| tttcaagcta taccaagcat acaatcaact atctcatata ca | 702 | |

<210> SEQ ID NO 9
<211> LENGTH: 1803
<212> TYPE: DNA
<213> ORGANISM: Artificial Sequence
<220> FEATURE:
<223> OTHER INFORMATION: Xylulokinase (XKS1)

<400> SEQUENCE: 9

| | | |
|---|---|---|
| atgttgtgtt cagtaattca gagacagaca agagaggttt ccaacacaat gtctttagac | 60 | |
| tcatactatc ttgggtttga tctttcgacc caacaactga aatgtctcgc cattaaccag | 120 | |
| gacctaaaaa ttgtccattc agaaacagtg gaatttgaaa aggatcttcc gcattataac | 180 | |
| acaagaagg gtgtctatat acacggcgac actatcgaat gtcccgtagc catgtggtta | 240 | |
| gaggctctag atctggttct ctcgaaatat cgcgaggcta aatttccatt gaacaaagtt | 300 | |
| atggccgtct cagggtcctg ccagcagcac gggtctgtct actggtcctc ccaagccgaa | 360 | |
| tctctgttag agcaattgaa taagaaaccg gaaaagatt tattgcacta cgtgagctct | 420 | |
| gtagcatttg caaggcaaac cgcccccaat tggcaagacc acagtactgc aaagcaatgt | 480 | |
| caagagtttg aagagtgcat aggtgggcct gaaaaaatgg ctcaattaac agggtccaga | 540 | |
| gcccatttta gatttactgg tcctcaaatt ctgaaaattg cacaattaga accagaagct | 600 | |
| tacgaaaaaa caaagaccat ttctttagtg tctaatttt tgacttctat cttagtgggc | 660 | |
| catcttgttg aattagagga ggcagatgcc tgtggtatga acctttatga tatacgtgaa | 720 | |
| agaaaattca gtgatgagct gctacatcta attgatagtt cttctaagga taaaactatc | 780 | |
| agacaaaaat taatgagagc acccatgaaa aatttgatag cgggtaccat ctgtaaatat | 840 | |
| tttattgaga agtacggttt caatacaaac tgcaaggtct ctcccatgac tggggataat | 900 | |
| ttagccacta tatgttcttt acccctgcgg aagaatgacg ttctcgtttc cctaggaaca | 960 | |
| agtactacag ttcttctggt caccgataag tatcaccct ctccgaacta tcatcttttc | 1020 | |
| attcatccaa ctctgccaaa ccattatatg ggtatgattg ttattgtaa tggttctttg | 1080 | |
| gcaagggaga ggataagaga cgagttaaac aaagaacggg aaaataatta tgagaagact | 1140 | |
| aacgattgga ctcttttaa tcaagctgtg ctagatgact cagaaagtag tgaaaatgaa | 1200 | |
| ttaggtgtat attttcctct gggggagatc gttcctagcg taaaagccat aaacaaaagg | 1260 | |
| gttatcttca atccaaaaag gggtatgatt gaaagagagg tggccaagtt caaagacaag | 1320 | |
| aggcacgatg ccaaaaatat tgtagaatca caggctttaa gttgcagggt aagaatatct | 1380 | |
| ccactgcttt cggattcaaa cgcaagctca aacagagac tgaacgaaga tacaatcgtg | 1440 | |
| aagtttgatt acgatgaatc tccgctgcgg gactacctaa ataaaaggcc agaaggact | 1500 | |
| ttttttgtag gtgggcttc taaaaacgat gctattgtga agaagtttgc tcaagtcatt | 1560 | |
| ggtgctacaa agggtaattt taggctagaa acaccaaact catgtgccct tggtggttgt | 1620 | |
| tataaggcca tgtggtcatt gttatacgac tctaataaaa ttgcagttcc ttttgataaa | 1680 | |
| tttctgaatg acaatttcc atggcatgta atggaaagca tatccgatgt ggataatgaa | 1740 | |

```
aattgggatc gctataattc caaaattgtc cccttaagcg aactggaaaa gactctcatc    1800
taa                                                                 1803

<210> SEQ ID NO 10
<211> LENGTH: 236
<212> TYPE: DNA
<213> ORGANISM: Artificial Sequence
<220> FEATURE:
<223> OTHER INFORMATION: Terminator of Alcohol Dehydrogenase (ADH1)

<400> SEQUENCE: 10
gcgaatttct tatgatttat gatttttatt attaaataag ttataaaaaa aataagtgta     60
tacaaatttt aaagtgactc ttaggtttta aaacgaaaat tcttattctt gagtaactct    120
ttcctgtagg tcaggttgct ttctcaggta tagcatgagg tcgctcttat tgaccacatc    180
tctaccggca tgccgagcaa atgcctgcaa atcgctcccc atttcaccca attgta        236

<210> SEQ ID NO 11
<211> LENGTH: 2043
<212> TYPE: DNA
<213> ORGANISM: Artificial Sequence
<220> FEATURE:
<223> OTHER INFORMATION: Transcetolase (TKL1)

<400> SEQUENCE: 11
atgactcaat ttactgacat tgataagcta gccgtctcca ccataagaat tttggctgtg     60
gacaccgtat ccaaggccaa ctcaggtcac ccaggtgctc cattgggtat ggcaccagct    120
gcgcacgttc tatggagtca aatgcgcatg aacccaacca acccagactg gatcaacaga    180
gatagatttg tcttgtctaa cggtcacgcg gtcgctttgt tgtattctat gctacatttg    240
actggttacg atctgtctat tgaagacttg aaacagttca gacagttggg ttccagaaca    300
ccaggtcatc ctgaatttga gttgccaggt gttgaagtta ctaccggtcc attaggtcaa    360
ggtatctcca cgctgttgg tatggccatg gctcaagcta accttgctgc cacttacaac    420
aagccaggct ttaccttgtc tgacaactac acctatgttt tcttgggtga cggttgtttg    480
caagaaggta tttcttcaga agcttcctcc ttggctggtc atttgaaatt gggtaacttg    540
attgccatct acgatgacaa caagatcact atcgatggtg ctaccagtat ctcattcgat    600
gaagatgttg ctaagagata cgaagcctac ggttgggaag ttttgtacgt agaaaatggt    660
aacgaagatc tagccggtat tgccaaggct attgctcaag ctaagttatc caaggacaaa    720
ccaactttga tcaaaatgac cacaaccatt ggttacggtt ccttgcatgc cggctctcac    780
tctgtgcacg gtgcccatt gaaagcagat gatgttaaac aactaaagag caaattcggt    840
ttcaacccag acagtccttt tgttgttcca caagaagttt acgaccacta ccaaagaca    900 atttaaagc aggtgtcga agccaacaac aagtggaaca gttgttcag cgaataccaa    960 aagaaattcc cagaattagg tgctgaattg gctagaagat gagcggcca actacccgca   1020 aattgggaat ctaagttgcc aacttacacc gccaaggact ctgccgtggc cactagaaaa   1080
ttatcagaaa ctgttcttga ggatgtttac aatcaattgc cagagttgat tggtggttct   1140 gccgattaa caccttctaa cttgaccaga tggaaggaag cccttgactt caaccctcct   1200
tcttccggtt caggtaacta ctctggtaga tacatcagat acggtattag agaacacgct   1260
atgggtgcca tcatgaacgg tatttcagct ttcggtgcca actacaaacc atacggtggt   1320
actttcttga acttcgtttc ttatgctgct ggtgccgtta gattgtccgc tttgtctggc   1380
```

```
cacccagtta tttgggttgc tacacatgac tctatcggtg tcggtgaaga tggtccaaca      1440
catcaaccta ttgaaacttt agcacacttc agatccctac caaacattca agtttggaga      1500
ccagctgatg gtaacgaagt ttctgccgcc tacaagaact ctttagaatc caagcatact      1560
ccaagtatca ttgctttgtc cagacaaaac ttgccacaat tggaaggtag ctctattgaa      1620
agcgcttcta agggtggtta cgtactacaa gatgttgcta acccagatat tattttagtg      1680
gctactggtt ccgaagtatc tttgagtgtt gaagctgcta agactttggc cgcaaagaac      1740
atcaaggctc gtgttgtttc tctaccagat ttcttcactt ttgacaaaca acccctagaa      1800
tacagactat cagtcttacc agacaacgtt ccaatcatgt ctgttgaagt tttggctacc      1860
acatgttggg gcaaatacgc tcatcaatcc ttcggtattg acagatttgg tgcctccggt      1920
aaggcaccag aagtcttcaa gttcttcggt ttcaccccag aaggtgttgc tgaaagagct      1980
caaaagacca ttgcattcta taagggtgac aagctaattt ctcctttgaa aaaagctttc      2040
taa                                                                    2043

<210> SEQ ID NO 12
<211> LENGTH: 717
<212> TYPE: DNA
<213> ORGANISM: Artificial Sequence
<220> FEATURE:
<223> OTHER INFORMATION: Ribose 5-Phosphate Epimerase (RPE1)

<400> SEQUENCE: 12
atggtcaaac caattatagc tcccagtatc cttgcttctg acttcgccaa cttgggttgc        60
gaatgtcata aggtcatcaa cgccggcgca gattggttac atatcgatgt catggacggc       120
cattttgttc caaacattac tctgggccaa ccaattgtta cctccctacg tcgttctgtg       180
ccacgccctg gcgatgctag caacacagaa aagaagccca ctgcgttctt cgattgtcac       240
atgatggttg aaaatcctga aaaatgggtc gacgattttg ctaaatgtgg tgctgaccaa       300
tttacgttcc actacgaggc cacacaagac ccttttgcat tagttaagtt gattaagtct       360
aagggcatca agctgcatg cgccatcaaa cctggtactt ctgttgacgt tttatttgaa       420
ctagctcctc atttggatat ggctcttgtt atgactgtgg aacctgggtt tggaggccaa       480
aaattcatgg aagacatgat gccaaaagtg gaaactttga gagccaagtt tccccatttg       540
aatatccaag tcgatggtgg tttgggcaag gagaccatcc cgaaagccgc caaagccggt       600
gccaacgtta ttgtcgctgg taccagtgtt ttcactgcag ctgacccgca cgatgttatc       660
tccttcatga agaagaagt ctcgaaggaa ttgcgttcta gagatttgct agattag           717

<210> SEQ ID NO 13
<211> LENGTH: 189
<212> TYPE: DNA
<213> ORGANISM: Artificial Sequence
<220> FEATURE:
<223> OTHER INFORMATION: 3-Phosphate Kinase Terminator (PGK1)

<400> SEQUENCE: 13
attgaattga attgaaatcg atagatcaat ttttttcttt tctctttccc catcctttac        60
gctaaaataa tagtttattt tattttttga atatttttta tttatatacg tatatataga       120
ctattattta tcttttaatg attattaaga tttttattaa aaaaaaattc gctcctcttt       180
taatgccctt                                                              189

<210> SEQ ID NO 14
<211> LENGTH: 984
```

```
<212> TYPE: DNA
<213> ORGANISM: Artificial Sequence
<220> FEATURE:
<223> OTHER INFORMATION: Aldose Reductase (GRE3)

<400> SEQUENCE: 14
atgtcttcac tggttactct taataacggt ctgaaaatgc ccctagtcgg cttagggtgc    60
tggaaaattg acaaaaaagt ctgtgcgagt caaatttatg aagctatcaa attaggctac   120
cgtctattcg atggtgcttg cgactacggc aacgaaaagg aagttggtga aggtatcagg   180
aaagccatct ccgaaggtct tgtttctaga aaggatatat tgttgtttc aaagttatgg    240 aacaattttc accatcctga tcatgtaaaa ttagctttaa agaagacctt aagcgatatg   300
ggacttgatt atttagacct gtattatatt cacttcccaa tcgccttcaa atatgttcca   360
tttgaagaga ataccctcc aggattctat acgggcgcag atgacgagaa aaaggtcac    420 atcaccgaag cacatgtacc aatcatagat acgtaccggg ctctggaaga atgtgttgat   480
gaaggcttga ttaagtctat tggtgttttcc aactttcagg aagcttgat tcaagattta   540 ttacgtggtt gtagaatcaa gcccgtggct ttgcaaattg aacaccatcc ttatttgact   600
caagaacacc tagttgagtt ttgtaaatta cacgatatcc aagtagttgc ttactcctcc   660
ttcggtcctc aatcattcat tgagatggac ttacagttgg caaaaaccac gccaactctg   720
ttcgagaatg atgtaatcaa gaaggtctca caaaaccatc caggcagtac cacttcccaa   780
gtattgctta atgggcaac tcagagaggc attgccgtca ttccaaaatc ttccaagaag   840
gaaaggttac ttggcaacct agaaatcgaa aaaagttca ctttaacgga gcaagaattg    900
aaggatattt ctgcactaaa tgccaacatc agatttaatg atccatggac ctggttggat   960
ggtaaattcc ccacttttgc ctga                                          984

<210> SEQ ID NO 15
<211> LENGTH: 1032
<212> TYPE: DNA
<213> ORGANISM: Artificial Sequence
<220> FEATURE:
<223> OTHER INFORMATION: CRE Recombinase

<400> SEQUENCE: 15
ctaatcgcca tcttccagca ggcgcaccat tgccctgtt tcactatcca gggtacggat    60
atagttcatg acaatattta cattggtcca gccaccagct tgcatgatct ccggtattga   120
aactccagcg cgggccatat ctcgcgcggc tccgacacgg gcactgtgtc cagaccaggc   180
caggtatctc tgaccagagt catccttagc gccgtaaatc aatcgatgag ttgcttcaaa   240
aatcccttcc agggcgcgag ttgatagctg gctggtggca gatggcgcgg caacaccatt   300
ttttctgacc cggcaaaaca ggtagttatt cggatcatca gctacaccag agacggaaat   360
ccatcgctcg accagtttag ttacccccag gctaagtgcc ttctctacac ctgcggtgct   420
aaccagcgtt ttcgttctgc caatatggat taacattctc ccaccgtcag tacgtgagat   480
atctttaacc ctgatcctgg caatttcggc tatacgtaac agggtgttat aagcaatccc   540
cagaaatgcc agattacgta tatcctggca gcgatcgcta ttttccatga gtgaacgaac   600
ctggtcgaaa tcagtgcgtt cgaacgctag agcctgtttt gcacgttcac cggcatcaac   660
gttttctttt cggatccgcc gcataaccag tgaaacagca ttgctgtcac ttggtcgtgg   720
cagcccggac cgacgatgaa gcatgtttag ctggcccaaa tgttgctgga tagttttac    780 tgccagaccg cgcgcctgaa gatatagaag ataatcgcga acatcttcag gttctgcggg   840
```

| | |
|---|---|
| aaaccatttc cggttattca acttgcacca tgccgcccac gaccggcaaa cggacagaag | 900 |
| cattttccag gtatgctcag aaaacgcctg gcgatccctg aacatgtcca tcaggttctt | 960 |
| gcgaacctca tcactcgttg catcgaccgg taatgcaggc aaattttggt gtacggtcag | 1020 |
| taaattggac at | 1032 |

<210> SEQ ID NO 16
<211> LENGTH: 327
<212> TYPE: DNA
<213> ORGANISM: Artificial Sequence
<220> FEATURE:
<223> OTHER INFORMATION: LTR of retrotransposon Ty1

<400> SEQUENCE: 16

| | |
|---|---|
| ctgagagatt ggtgaatttt gagatgattg taggcattcc attgttgatc aaggctacaa | 60 |
| tattatgtat acagaatata ctaaaagttc cctcgaggg tagaggaatc ctcaaagggg | 120 |
| aagcgatatt tctacataat attattacga ttattcctca ttccgtttta tatgtttcat | 180 |
| tatcctatta cattatcaat ccttgcactt cagcttcctc taacttcgat gacagtttct | 240 |
| cataccttat gtcatcgtct aacaccgtat atgataatat actggtagtg tgactactag | 300 |
| tttatagacg atagttgatt tttattc | 327 |

<210> SEQ ID NO 17
<211> LENGTH: 2216
<212> TYPE: DNA
<213> ORGANISM: Artificial Sequence
<220> FEATURE:
<223> OTHER INFORMATION: LEU2 (ORF + promoter and terminator)

<400> SEQUENCE: 17

| | |
|---|---|
| tcgaggagaa cttctagtat atccacatac ctaatattat tgccttatta aaatggaat | 60 |
| cccaacaatt acatcaaaat ccacattctc ttcaaaatca attgtcctgt acttccttgt | 120 |
| tcatgtgtgt tcaaaaacgt tatatttata ggataattat actctatttc tcaacaagta | 180 |
| attggttgtt tggccgagcg gtctaaggcg cctgattcaa gaaatatctt gaccgcagtt | 240 |
| aactgtggga atactcaggt atcgtaagat gcaagagttc gaatctctta gcaaccatta | 300 |
| tttttttcct caacataacg agaacacaca ggggcgctat cgcacagaat caaattcgat | 360 |
| gactggaaat tttttgttaa tttcagaggt cgcctgacgc atataccttt ttcaactgaa | 420 |
| aaattgggag aaaaaggaaa ggtgagaggc cggaaccggc ttttcatata aatagagaa | 480 |
| gcgttcatga ctaaatgctt gcatcacaat acttgaagtt gacaatatta tttaaggacc | 540 |
| tattgttttt tccaataggt ggttagcaat cgtcttactt tctaactttt cttaccttt | 600 |
| acatttcagc aatatatata tatatttcaa ggatatacca ttctaatgtc tgcccctaag | 660 |
| aagatcgtcg ttttgccagg tgaccacgtt ggtcaagaaa tcacagccga agccattaag | 720 |
| gttcttaaag ctatttctga tgttcgttcc aatgtcaagt tcgatttcga aaatcattta | 780 |
| attggtggtg ctgctatcga tgctacaggt gtcccacttc cagatgaggc gctggaagcc | 840 |
| tccaagaagg ttgatgccgt tttgttaggt gctgtgggtg gtcctaaatg gggtaccggt | 900 |
| agtgttagac tgaacaagg tttactaaaa atccgtaaag aacttcaatt gtacgccaac | 960 |
| ttaagaccat gtaactttgc atccgactct cttttagact tatctccaat caagccacaa | 1020 |
| tttgctaaag gtactgactt cgttgttgtc agagaattag tgggaggtat ttactttggt | 1080 |
| aagagaaagg aagacgatgg tgatggtgtc gcttgggata tgaacaata caccgttcca | 1140 |
| gaagtgcaaa gaatcacaag aatggccgct ttcatggccc tacaacatga gccaccattg | 1200 |

```
cctatttggt ccttggataa agctaatgtt ttggcctctt caagattatg gagaaaaact   1260
gtggaggaaa ccatcaagaa cgaattccct acattgaagg ttcaacatca attgattgat   1320
tctgccgcca tgatcctagt taagaaccca acccacctaa atggtattat aatcaccagc   1380
aacatgtttg gtgatatcat ctccgatgaa gcctccgtta tcccaggttc cttgggtttg   1440
ttgccatctg cgtccttggc ctctttgcca gacaagaaca ccgcatttgg tttgtacgaa   1500
ccatgccacg gttctgctcc agatttgcca aagaataagg ttgaccctat cgccactatc   1560
ttgtctgctg caatgatgtt gaaattgtca ttgaacttgc ctgaagaagg taaggccatt   1620
gaagatgcag ttaaaaaggt tttggatgca ggtatcagaa ctggtgattt aggtggttcc   1680
aacagtacca ccgaagtcgg tgatgctgtc gccgaagaag ttaagaaaat ccttgcttaa   1740
aaagattctc ttttttttatg atatttgtac ataaacttta taaatgaaat tcataataga   1800
aacgacacga aattacaaaa tggaatatgt tcatagggta gacgaaacta tatacgcaat   1860
ctacatacat ttatcaagaa ggagaaaaag gaggatagta aaggaataca ggtaagcaaa   1920
ttgatactaa tggctcaacg tgataaggaa aaagaattgc actttaacat taatattgac   1980
aaggaggagg gcaccacaca aaaagttagg tgtaacagaa aatcatgaaa ctacgattcc   2040
taatttgata ttggaggatt ttctctaaaa aaaaaaaaat acaacaaata aaaaacactc   2100
aatgacctga ccatttgatg gagtttaagt caataccttc ttgaaccatt tcccataatg   2160
gtgaaagttc cctcaagaat tttactctgt cagaaacggc cttacgacgt agtcga       2216
```